US008859267B2

(12) United States Patent
Seyama et al.

(10) Patent No.: US 8,859,267 B2
(45) Date of Patent: Oct. 14, 2014

(54) CHIP FOR OPTICAL ANALYSIS

(75) Inventors: Michiko Seyama, Atsugi (JP); Serge Camou, Atsugi (JP); Yuzuru Iwasaki, Atsugi (JP); Toru Miura, Atsugi (JP); Jyunichi Takahashi, Atsugi (JP); Tsuneyuki Haga, Atsugi (JP); Tsutomu Horiuchi, Atsugi (JP)

(73) Assignee: Nippon Telegraph and Telephone Corporation, Tokyo (JP)

( * ) Notice: Subject to any disclaimer, the term of this patent is extended or adjusted under 35 U.S.C. 154(b) by 1706 days.

(21) Appl. No.: 12/304,112

(22) PCT Filed: Jun. 11, 2007

(86) PCT No.: PCT/JP2007/061757
§ 371 (c)(1),
(2), (4) Date: Jun. 10, 2010

(87) PCT Pub. No.: WO2007/145180
PCT Pub. Date: Dec. 21, 2007

(65) Prior Publication Data
US 2010/0248351 A1 Sep. 30, 2010

(30) Foreign Application Priority Data

Jun. 12, 2006 (JP) ................................. 2006-162879
Jun. 14, 2006 (JP) ................................. 2006-165172
Jun. 26, 2006 (JP) ................................. 2006-175682

(51) Int. Cl.
*C12M 1/40* (2006.01)
*G01N 21/01* (2006.01)
*B01L 3/00* (2006.01)
*G01N 21/55* (2014.01)

(52) U.S. Cl.
CPC ....... *G01N 21/553* (2013.01); *B01L 2300/0864* (2013.01); *B01L 2300/0645* (2013.01); *B01L 2300/069* (2013.01); *B01L 2300/0861* (2013.01); *B01L 2200/148* (2013.01); *B01L 2400/084* (2013.01); *B01L 2300/0816* (2013.01); *B01L 2300/0825* (2013.01); *B01L 3/502715* (2013.01)

USPC .................... 435/288.7; 435/287.2; 422/504; 356/244; 436/518

(58) Field of Classification Search
USPC ............. 356/244; 435/288.7, 287.2; 422/504; 436/518
See application file for complete search history.

(56) References Cited

U.S. PATENT DOCUMENTS

| 6,779,559 B2 * | 8/2004 | Parce et al. .................... 137/806 |
| 6,858,185 B1 * | 2/2005 | Kopf-Sill et al. ............. 422/504 |
| 2003/0017579 A1 * | 1/2003 | Corn et al. ................. 435/287.2 |

FOREIGN PATENT DOCUMENTS

| EP | 0343826 | 11/1989 |
| EP | 1 643 237 | 4/2006 |

(Continued)

OTHER PUBLICATIONS

Supplementary European Search Report from related Application No. EP 07745046 dated Nov. 23, 2009 (9 pages).

(Continued)

*Primary Examiner* — William H Beisner
*Assistant Examiner* — Danielle Henkel
(74) *Attorney, Agent, or Firm* — Workman Nydegger

(57) ABSTRACT

The present invention relates to a chip for optical analysis. In particular, the present invention relates to an optical sensor handling a liquid sample, which is a chip for analysis that can be used for selectively measuring a biologically-relevant substance or a chemical substance such as an environmental pollutant or a health affecting substance in a liquid to be measured. The chip for optical analysis of the present invention is characterized in that (1) an adsorption region (filter region) is provided between a sample introduction section and the observation section in a passage of the chip for analysis, (2) a bypass passage is provided in the passage (main passage) of the chip for analysis, and a time lag is generated between samples passed through the main passage and passed through a bypass passage, and (3) a measurement region and a reference region are provided in the observation section of the chip for analysis. In the present invention, the aspects (1) to (3) can be achieved individually or two or more thereof can be combined.

23 Claims, 24 Drawing Sheets

(56) References Cited

FOREIGN PATENT DOCUMENTS

| JP | 2002-214131   | 7/2002  |
|----|---------------|---------|
| JP | 2002-214141 A | 7/2002  |
| JP | 2003-121350 A | 4/2003  |
| JP | 2004-053372 A | 2/2004  |
| JP | 2005-283145 A | 10/2005 |
| JP | 2006-098345 A | 4/2006  |

OTHER PUBLICATIONS

European Search Report from related Application No. EP 11150986.5 dated Mar. 2, 2011.

PCT Notification of Transmittal of Translation of the International Preliminary Report on Patentability (Chapter 1 or Chapter II of the Patent Cooperation Treaty) of related Japanese Application No. PCT/JP2007/061757, dated Dec. 31, 2008 (7 pages).

* cited by examiner

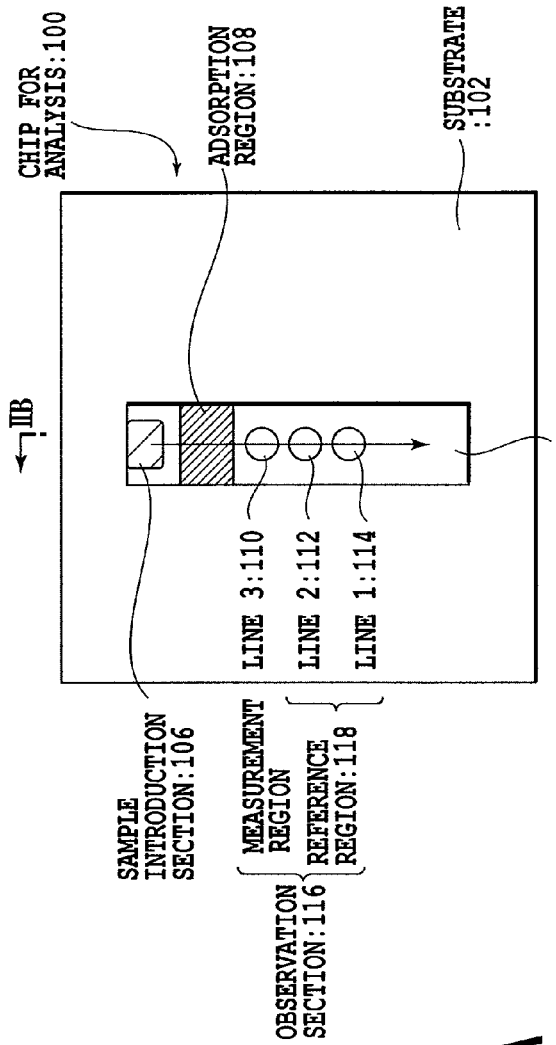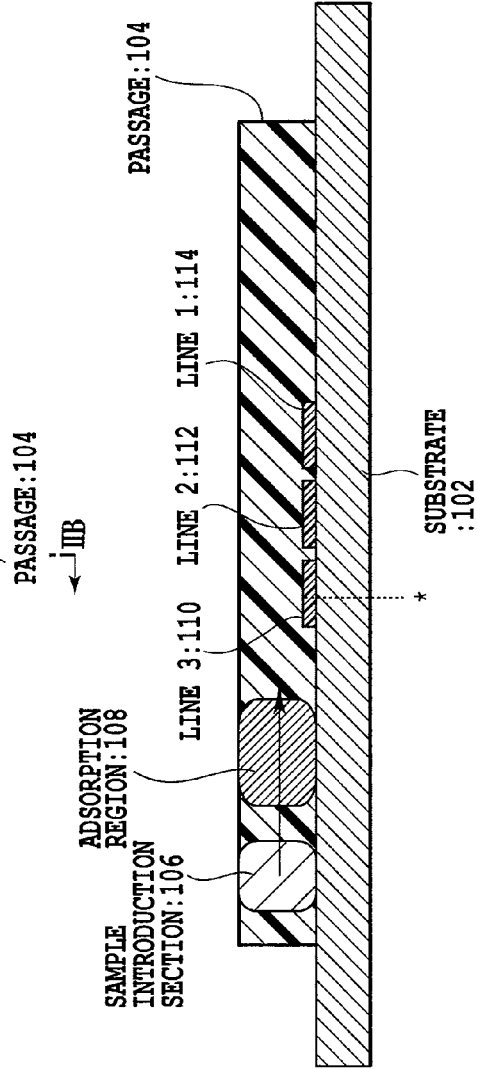
FIG.2A
FIG.2B

CHANGE OVER TIME IN SAMPLE (MEASUREMENT OBJECT)
CONTENT IN SOLUTION REACHING POSITION OF * ON PASSAGE

SEQUENCE LISTING

```
<160> NUMBER OF SEQ ID NOS: 3

<210> SEQ ID NO 1
<211> LENGTH: 23
<212> TYPE: DNA
<213> ORGANISM: Artificial Sequence
<220> FEATURE:
<223> OTHER INFORMATION: This sequence was artificially synthesized.

<400> SEQUENCE: 1
cctctgactt caacagcgac act                                        23

<210> SEQ ID NO 2
<211> LENGTH: 23
<212> TYPE: DNA
<213> ORGANISM: Artificial Sequence
<220> FEATURE:
<223> OTHER INFORMATION: This sequence was artificially synthesized.

<400> SEQUENCE: 2
cctcagactt caacagggac act                                        23

<210> SEQ ID NO 3
<211> LENGTH: 26
<212> TYPE: DNA
<213> ORGANISM: Artificial Sequence
<220> FEATURE:
<223> OTHER INFORMATION: This sequence was artificially synthesized.

<400> SEQUENCE: 3
ggagactgaa gttgtcgctg tgggtg                                     26
```

CHIP FOR OPTICAL ANALYSIS

TECHNICAL FIELD

The present invention relates to a chip for optical analysis. In particular, the present invention relates to a chip for analysis, which can be used for an optical sensor for handling a liquid sample that selectively measures chemical substances such as a biologically-relevant substance or an environmental pollutant or a health affecting substance in a liquid to be measured. The chip for analysis of the present invention can use a substance having molecular selectivity. Furthermore, the chip for analysis of the present invention measures a real sample containing impurities, with higher measurement sensitivity and higher precision in measurement. The chip for analysis of the present invention is intended for a simpler operation in measurement and higher sensitivity and higher precision in measurement.

BACKGROUND ART

The method for measuring a chemical substance in a liquid sample include for example electric and optical measurement methods in which a substance having molecular selectivity is immobilized beforehand, a liquid sample is allowed to flow thereon, and a bound molecule is selectively detected.

Optical methods involve techniques using a probe molecule to which a fluorescent substance or a light-absorbing substance is immobilized beforehand. In addition, methods using a total reflection optical system are available by which binding of a molecule and an immobilized substance having molecular selectivity can be directly observed. These methods are known as methods in which an excited evanescent wave is used as a probe light, and binding in the vicinity of the surface is directly measured with high sensitivity. Most commonly used method among the total reflection-type optical systems is Surface Plasmon Resonance (SPR) measurement method, which utilizes a sample's absorption of a surface plasmon excited by total reflection of a metal thin film formed on a substrate surface, and total reflection-type attenuation measurement method, which utilizes a sample's absorption of an evanescent wave excited by total reflection due to a difference between a substrate surface and a sample in a refractive index.

To measure a liquid sample with a total reflection optical system, means of forming a passage on a substrate and immobilizing a probe molecule in the passage beforehand or forming a passage on an immobilized probe molecule is taken. Then, a liquid sample is passed through this passage. Based on an interaction between the immobilized probe molecule and a substance to be measured in a sample, whether the substance to be measured is contained in the sample can be determined, and the substance to be measured can be further quantified using the above-mentioned total reflection optical system (for example, the amount of a specific chemical substance contained in a liquid can be determined from the condition of a reflected light of a measurement light irradiated on the above-mentioned passage).

Furthermore, measurement using a total reflection optical system and a substance having molecular selectivity appears to be more suitable for short-time low-cost screening that is also suitably used in a field test than high-cost, high-precision, and high-sensitivity analyses represented by chromatography. A simple device for total reflection optical measurement has already been developed and described in, for example, Patent Document 1.

[Patent Document 1] Japanese Patent Laid-Open No. 2002-214131

DISCLOSURE OF THE INVENTION

To conduct a high-sensitivity analysis in optical measurement, preparation of a reference sample, which does not contain a measurement object and serves as a reference, is required. While it is possible to separately prepare a sample not containing a substance to be measured as a reference for a real sample, which contains a substance to be measured, a sample obtained by removing the substance to be measured from the real sample itself is considered to be ideal as a reference. From this viewpoint, a reference sample obtained by removing a substance to be measured from a real sample is prepared and used as a reference in some cases. However, when this reference sample is prepared, a complex pretreatment operation may be required, and such necessity of a pretreatment operation is not desirable in on-site or simple measurement.

Furthermore, for example, when a sample to be actually measured such as serum, blood, urine, an animal body fluid other than these, environmental water, or a liquid collected from a plant is a liquid sample, many impurities exist in such a liquid sample in addition to the substance to be measured. When total reflection optical measurement is performed, it is necessary to eliminate effects of such impurities and selectively detect the substance to be measured. In consideration of on-site measurement, such elimination treatment of impurities is not desirable either.

Such measurement by a total reflection optical system in which a probe molecule is immobilized on a substrate beforehand as described above suffers from a problem that many impurities are adsorbed or accumulated in a space on a substrate in which a measurement region is provided. Conventionally, when such accumulation of impurities occurs due to adsorption, effects of impurities are suppressed to some extent by using a region in which a probe molecule is not immobilized as a reference region, performing differential measurement between a measurement region and the reference region, and deducting changes other than a reaction by a probe molecule. However, when a measurement object having a low concentration is to be detected, adsorption and accumulation of impurities in the reference region in which a probe molecule does not exist often differ from those in the measurement region. Therefore, a problem arises that, even if a difference between the reference region and the measurement region is deducted, effects of impurities cannot be eliminated, a baseline for measurement changes, and the baseline changes more greatly than a signal to be detected.

Furthermore, devices by which a change in the refractive index of a sample is read from a change in the resonance angle are commonly used in surface plasmon resonance measurement methods. However, since the refractive index of a liquid sample is greater than that of a gas, the resonance angle may change about 15 to 20 degrees after introduction of a sample. Such a great change in the resonance angle can be detected with an analytical device for a laboratory, which has a mobile detection system. In a simple device without moving parts, however, it is impossible to detect a resonance angle in a condition where a sample is not introduced, and a signal cannot be obtained. On the contrary, a problem arises that, even if a device has a mobile detection system, rapid measurement is impossible because the detection operation requires time.

An object of the present invention is to provide a chip for optical analysis which can very easily and conveniently determine how a measurement object is contained in a liquid to be measured by preparing a reference sample from the liquid to be measured as a reference.

Furthermore, another object of the present invention is to provide a chip for optical analysis which can prepare a reference sample in which a substance to be measured is free and selectively detect a measurement object in the real sample only by introducing a real sample into the chip for analysis.

Furthermore, another object of the present invention is to provide a chip for analysis which can suppress a signal noise generated from a difference in adsorption or accumulation of impurities to a measurement region and a reference region in a measurement method for detecting a substance to be measured based on an interaction between a probe molecule immobilized on a substrate and the substance to be measured, for example, a measurement method using a total reflection optical system. Even when a liquid sample to be measured by the chip for analysis of the present invention contains many impurities, measurement using a total reflection optical system can be achieved with higher sensitivity and higher precision.

The present invention relates to a chip for optical analysis. The chip for optical analysis of a first embodiment is a chip for optical analysis provided with a substrate and a passage on the substrate, wherein the passage comprises a sample introduction section, an observation section, and an adsorption region for adsorbing a substance to be measured between the sample introduction section and the observation section.

The chip for optical analysis further comprises a passage that bypasses the adsorption region from the sample introduction section to the observation section, so that a sample passed through the bypass passage can reach the observation section taking more time than a sample passed through the adsorption region. In the chip for optical analysis of the present invention, the observation section can comprise at least a measurement region for detecting a substance to be measured and a reference region.

On the measurement region, a material which is an antibody, an antigen, an enzyme, an oligonucleotide, a DNA, an RNA, a modified cyclodextrin, or a naturally occurring or synthesized cyclic compound that functions as an ionophore can be immobilized.

The adsorption region can contain protein A, dextran or a modified product thereof, silica having an organic coating, or alumina having an organic coating as an adsorbent.

The chip for optical analysis can further have a metal thin film between the substrate and the passage. In the chip for optical analysis, the passage and/or bypass passage may be a porous membrane.

The chip for optical analysis of another embodiment comprises a substrate that is transparent to a measurement light, a chip main body joined to a surface of the substrate, an introduction port formed in the chip main body for introducing a liquid to be measured, a first passage through which a liquid to be measured introduced through the introduction port passes, an observation section arranged between the substrate and the chip main body in the first passage and irradiated with the measurement light, a metal thin film layer positioned at the observation section and provided on a wall surface of the first passage, a second passage branched from the first passage and merged again into the first passage on the upstream side of the observation section, an adsorption region for capturing a predetermined component contained in a liquid to be measured, the adsorption region positioned between a branching section and a merging section with the second passage and incorporated in the first passage, and means for generating a difference in time to reach the observation section so that the liquid to be measured reaches the observation section from the branching section through the first passage earlier than reaching the observation section from the branching section through the second passage.

The chip main body can further comprise a liquid absorbing and holding section incorporated in this chip for optical analysis and connected to the first passage on the downstream side of the observation section to absorb the liquid to be measured passed through the observation section.

The observation section can comprise at least a measurement region for detecting a substance to be measured and a reference region.

In the chip for optical analysis of this embodiment, the means for generating a difference in time to reach the measurement region may be (a) a hydrophilically treated layer formed on a wall surface of the second passage, (b) at least one passage resistance-increasing block projected from the surface of the substrate facing the second passage into the second passage, (c) a setting of the volume of the second passage larger than that of the first passage from the branching section through the merging section, or (d) a liquid collecting section provided halfway through the second passage for collecting the liquid to be measured.

Furthermore, in the chip for optical analysis of this embodiment, a material having molecular selectivity may be immobilized on the measurement region of the first passage. The material having molecular selectivity can contain at least one material selected from the group consisting of an antibody, an antigen, an enzyme, an oligonucleoside, a ribonucleoside, and a modified cyclodextrin compound. Furthermore, in the chip for optical analysis of this embodiment, the adsorption region can contain at least one adsorbent selected from a dextran gel using protein A as a modifier, organic membrane-coated silica, and organic membrane-coated alumina.

In each of the chips for optical analysis of the embodiments, on the measurement region, a first substance having molecular selectivity that selectively interacts with a specific molecule is immobilized, and on the reference region, a second substance having molecular selectivity which is different only in selectivity to the specific molecule with which the first substance having molecular selectivity interacts and is comparable to the first substance having molecular selectivity in other characteristics is immobilized, and the first substance having molecular selectivity and the second substance having molecular selectivity can be immobilized on the substrate by the same method.

The chip for optical analysis of another embodiment of the present invention is a chip for analysis, comprising a substrate, a metal thin film on the substrate, and an observation section on the metal thin film, wherein the observation section is provided with a measurement region and a reference region, and on the measurement region, a first substance having molecular selectivity that selectively interacts with a specific molecule is immobilized, and on the reference region, a second substance having molecular selectivity that is different only in selectivity to the specific molecule with which the first substance having molecular selectivity interacts and is comparable to the first substance having molecular selectivity in other characteristics is immobilized, and the first substance having molecular selectivity and the second substance having molecular selectivity can be immobilized on the substrate by the same method.

In each of the chips for optical analysis of the above-mentioned embodiments of the present invention, the first substance having molecular selectivity and the second substance having molecular selectivity are preferably antibodies or antigens, which are of the same kinds. It is preferable that the second substance having molecular selectivity is obtained by inactivating the first substance having molecular selectivity, and the inactivation is achieved by irradiation of a high energy ray selected from an X-ray, a gamma-ray, or an electron beam, heat treatment, electrochemical oxidation or reduction, or contact with an acidic or alkaline buffer. Furthermore, it is preferable that the first substance having molecular selectivity and the second substance having molecular selectivity are DNA, and that the second substance having molecular selectivity is obtained by replacing 10% or less of nucleotides constituting the first substance having molecular selectivity.

In each of the chips for optical analysis of the above-mentioned embodiments of the present invention, two or more observation sections each comprising the measurement region and the reference region as one set are provided in the passage on the substrate, and the first substances having molecular selectivity different from each other are immobilized on the measurement region of the observation sections, so that each observation section can detect a different molecule.

The chip for optical analysis according to the present invention can prepare a reference sample in which a substance to be measured is free only by introducing a liquid sample containing the substance to be measured into the sample introduction section, and can measure the reference sample and a real sample containing this substance to be measured. Furthermore, according to the present invention, DNA, RNA, ions, amino acids, and peptides can be easily sensed with high sensitivity.

Since the chip for optical analysis of the present invention is provided with the means for allowing a liquid to be measured to reach the observation section from the branching section through the first passage earlier than reaching the observation section from the branching section through the second passage, the reference sample that is passed through a filter reaches the observation section first. Therefore, even when a simple surface plasmon resonance measurement device is used, a signal serving as the reference of a measured value can be first obtained, and then the liquid to be measured that is passed through the second passage reached the observation section, resulting in an accurate analysis of the liquid to be measured. In the chip for optical analysis of the present invention, the observation section can be provided with a measurement region and a reference region. With such a structure, a reference sample can be prepared only by supplying the liquid to be measured from the introduction port into the first passage, and a measurement object can be detected and quantified based on an interaction between a material having molecular selectivity immobilized on the measurement region and the measurement object.

According to the present invention, a change in the baseline that occurs at the time of measurement of a real sample containing many impurities can be minimized, and a small amount of a substance to be measured in a sample containing many impurities can be detected.

BRIEF DESCRIPTION OF THE DRAWINGS

FIG. 2A is a planar schematic diagram showing a chip for optical analysis of one embodiment of the present invention;

FIG. 2B is a cross-sectional schematic diagram showing the chip for optical analysis of one embodiment of the present invention;

BEST MODE FOR CARRYING OUT THE INVENTION

Embodiments in which the chip for optical analysis according to the present invention is applied to an analysis of a liquid sample using a surface plasmon resonance measurement device will be explained in detail with reference to the drawings. The scope of the present invention is not limited to these embodiments, these embodiments can be combined, and the concepts of the present invention described in claims that fall within the scope of the present invention can be changed or modified. In other words, it is noted that the present invention can be naturally applied to other arbitrary techniques attributable to the spirit thereof. For example, the present invention can be applied not only to surface plasmon resonance measurement devices, but also to sensing by a total reflection type optical assay system using a material having molecular selectivity as a probe molecule, for example, attenuated total reflection type measurement methods using an ultraviolet light, a visible light, or an infrared light, absorption/emission spectrometry utilizing total reflection light excitation, and the like.

Figure 1:
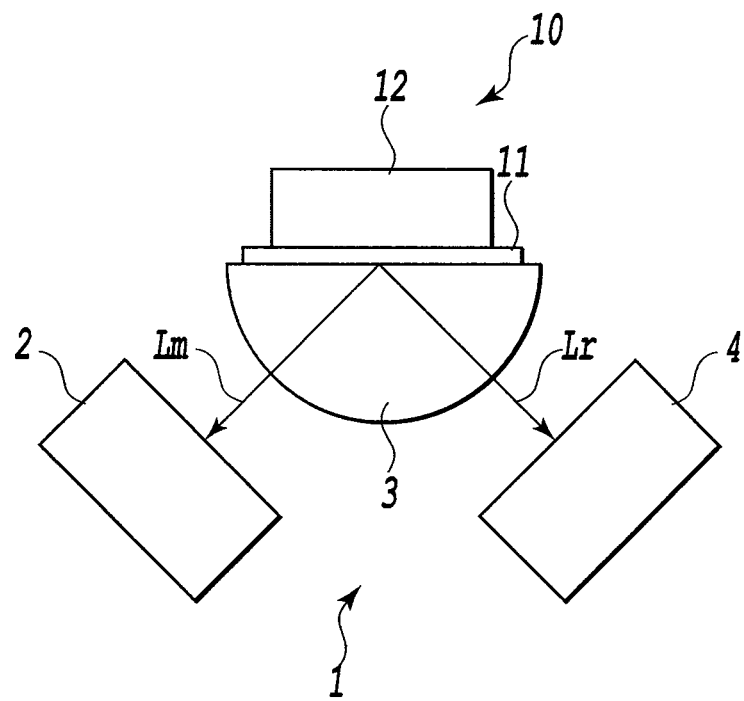
FIG. 1 is a schematic diagram of a surface plasmon resonance measurement device using the chip for optical analysis according to the present invention.

The concept of the surface plasmon resonance measurement device is shown in FIG. 1. The surface plasmon resonance measurement device 1 has a light source 2 for irradiating the measurement region of a chip for optical analysis 10 with a measurement light Lm, a semicylindrical collecting lens (cylindrical prism) 3 overlapped with the chip for optical analysis 10 via a matching oil, a light detector 4 for detecting a reflected light Lr reflected on the measurement region of the chip for optical analysis 10, and a signal processing section (not shown) for processing a signal detected by this light detector 4.

A light from the light source 2 is linearly focused with the collecting lens 3 and irradiated on the measurement region of the chip for optical analysis 10. A polarizer (not shown) is placed between the collecting lens 3 and either the light source 2 or the detector 4 to detect only a p-polarized component. The reflected light Lr is guided to the light detector 4 through the collecting lens 3 again, the signal is processed at the signal processing section (not shown), and a liquid to be measured supplied to the chip for optical analysis 10 is analyzed. The chip for optical analysis 10 shown in FIG. 1 comprises a substrate 11 and a chip main body 12 joined to a surface of the substrate 11.

Hereafter, such a chip for optical analysis as described above will be explained. The chip for optical analysis of the present invention can be classified into the following aspects.

(1) An adsorption region (filter region) is provided between a sample introduction section and an observation section in the passage of the chip for optical analysis. Consequently, a measurement object is initially adsorbed in the adsorption region, and a reference sample reaches the observation section. Subsequently, when the adsorption region is saturated with the measurement object, or adsorption of the measurement object is stopped, a sample containing the measurement object reaches the observation section, and the measurement object can be observed.

(2) The passage of the chip for optical analysis (main passage) is provided with a bypass passage to generate a time lag between samples passed through the main passage and the bypass passage. In this aspect, it is preferable to further provide the main passage with an adsorption region (filter region). In this aspect, a measurement object is adsorbed in the adsorption region in the main passage, and a reference sample reaches the observation section. Meanwhile, a sample containing the measurement object is allowed to flow through the bypass passage and reaches the observation section later than the reference sample flowing through the main passage.

(3) An observation section of the chip for optical analysis is provided with a measurement region and a reference region. In this aspect, a substance having molecular selectivity is immobilized on the measurement region, and a substance which does not have molecular selectivity and is comparable to those of the substance having molecular selectivity immobilized on the measurement region in other characteristics is immobilized on the reference region. In this aspect, a sample solution containing impurities is allowed to flow through the measurement region and the reference region at the same time, and impurities are adsorbed to or accumulated in the measurement region and the reference region at the same time. As a result, when a difference between the measurement region and the reference region is measured, effects of adsorption and accumulation of impurities are offset, and a change in the baseline for measurement is minimized.

In the present invention, the above-mentioned aspects (1) to (3) can be implemented individually, or two or more thereof can be combined.

Hereafter, the chip for optical analysis according to the first embodiment and the second embodiment of the present invention will be explained. The first embodiment corresponds to an aspect of a combination of the above-described (1) and (3). The second embodiment corresponds to an aspect of a combination of the above-described (2) and (3) where an adsorption region is provided.

The chip for optical analysis according to the first embodiment is a chip for optical analysis comprising a substrate and a passage composed of a porous membrane on the substrate, wherein the passage comprises a sample introduction section, an observation section, and an adsorption region for adsorbing a substance to be measured between the sample introduction section and the observation section, and the observation section comprises at least a measurement region for detecting a substance to be measured and a reference region.

The chip for optical analysis according to the second embodiment further comprises a passage that bypasses the adsorption region from the sample introduction section to the observation section, so that a sample passed through the bypass passage should reach the observation section taking more time than a sample passed through the adsorption region.

Hereafter, the present invention will be explained with reference to the drawings.

FIGS. 2A and 2B show the chip for optical analysis 100 according to the first embodiment of the present invention. FIG. 2A is a planar view, and FIG. 2B is a cross-sectional view at IIB-IIB.

The chip for optical analysis of the present invention includes a passage 104 composed of a porous membrane on a substrate 102. A sample introduction section 106 for delivering a sample by drops is provided at one end of this passage. The sample introduction section is not limited so long as it has a structure that enables delivery of a liquid sample by drops, and does not need to be formed as a distinct region that can be distinguished from other regions of the passage. Therefore, it is preferable to form this section with the same material as that of the passage. Furthermore, the passage is provided with an observation section 116 comprising lines 1 to 3 (114, 112, 110). The observation section 116 comprises a reference region 118 comprising lines 1 and 2 (114, 112) and a measurement region for detecting a substance to be measured (110 in FIGS. 2A and 2B). FIGS. 2A and 2B show an example of the reference region provided with two types of lines, but a line of one type may be provided. Furthermore, the passage is provided with an adsorption region 108 for adsorbing a substance to be measured between the sample introduction section and the observation section. An adsorbent immobilized on the adsorption region may selectively adsorb the substance to be measured or adsorb two or more substances containing the substance to be measured.

On the measurement region, a substance having molecular selectivity that selectively binds to a substance to be measured is immobilized. Specific examples thereof include materials which are antibodies, antigens, enzymes, oligonucleotides, DNA, RNA, modified cyclodextrin, or naturally occurring or synthesized cyclic compounds that function as ionophores. For example, when a human IgG antigen is detected, it is sufficient to immobilize an anti-human IgG.

A reference substance that does not bind to a substance to be measured but is similar to a substance having molecular selectivity is immobilized on the reference region. For example, it is sufficient to immobilize a reference substance that causes a different interaction between the substance having molecular selectivity immobilized on the measurement region and the substance to be measured. Specifically, for example, when an antibody (for example, an anti-human IgG) is immobilized on the measurement region, it is sufficient to immobilize an antibody of an origin or species different from that of this antibody (for example, anti-goat IgG) on the reference region. As shown in FIGS. 2A and 2B, when the reference region is provided with two lines, it is preferable to immobilize such a reference substance as described above on one of these lines and form a portion composed of a material not containing the substance having molecular selectivity or the reference substance such as a blocking agent (for example, bovine serum albumin) on the other line. By doing this, detection can be achieved with higher precision when a blocking agent is applied to the measurement region and the region on which the reference substance is immobilized.

When the reference region is provided with a line of one type, a reference substance may be immobilized on the line as described above, or a line not containing a substance having molecular selectivity or a reference substance may be formed.

On the adsorption region, a material that can adsorb a substance to be measured is immobilized as an adsorbent. For example, a material that can adsorb a substance to be measured, such as protein A, dextran or a modified product thereof, for example, dextran gel using protein A as a modifier or modified dextran microparticles, silica having an organic material coating, and alumina having an organic material coating, is used. The adsorbent may adsorb two or more substances including the substance to be measured.

The material used for the passage is not particularly limited so long as a liquid sample can move from the sample introduction section to the observation section without using a special operation such as suction, and a porous membrane can be formed thereon. For example, cellulose or a cellulose derivative such as cellulose acetate or nitrocellulose can be used.

The substrate is not particularly limited so long as it is made of a material that is transparent to a light used in a measurement device (for example, a surface plasmon resonance [SPR] device) on which the chip for optical analysis is mounted, and any material can be used. For example, a glass substrate, a plastic substrate, or the like can be used.

Although not shown in FIGS. 2A and 2B, it is preferable that the chip for optical analysis of the present invention comprises a metal thin film between the substrate and the passage. For the metal thin film, for example, a material such as gold can be used. By providing a metal thin film such as a gold thin film, the chip for optical analysis of the present invention can be used as an analysis chip for a surface plasmon resonance device.

The operation of the chip for optical analysis of the first embodiment will be explained. After a liquid sample containing a substance to be measured is introduced into the chip for optical analysis from the sample introduction section, the liquid sample is allowed to flow along the passage in the direction of the observation section due to capillary phenomenon of a porous material forming the passage. When the liquid sample is allowed to flow, first, the liquid sample reaches the adsorption region in which an adsorbent exists. Since the adsorption region contains an adsorbent for adsorbing the substance to be measured, the substance to be measured is adsorbed, and other substances flow to the observation region. Here, since the liquid sample flowing to the observation region does not contain the substance to be measured any longer, it means that a reference sample has reached the observation region.

When the liquid sample is further allowed to flow, the adsorbent of the adsorption region is saturated and does not adsorb the substance to be measured any longer since the amount of the adsorbent of the adsorption region is limited. In this state, the substance to be measured reaches the observation region, and the substance to be measured can be measured.

Thus, in the chip for optical analysis of the first embodiment, the reference sample reaches the observation section immediately after the introduction of the liquid sample which includes until the time when the adsorption region is saturated with the substance to be measured. This measurement result of the reference sample immediately after the introduction of the liquid sample serves as the baseline for measurement. Subsequently, after an elapse of time, the liquid sample containing the substance to be measured reaches the observation section, and the substance to be measured is measured.

For the chip for optical analysis of the present invention, a reference sample does not need to be separately prepared, and both a signal as the baseline for measurement and a measurement signal of a sample containing the substance to be measured can be measured sequentially only by an operation of introducing a liquid sample containing the substance to be measured into the chip for optical analysis.

Figures 3A, 3B:
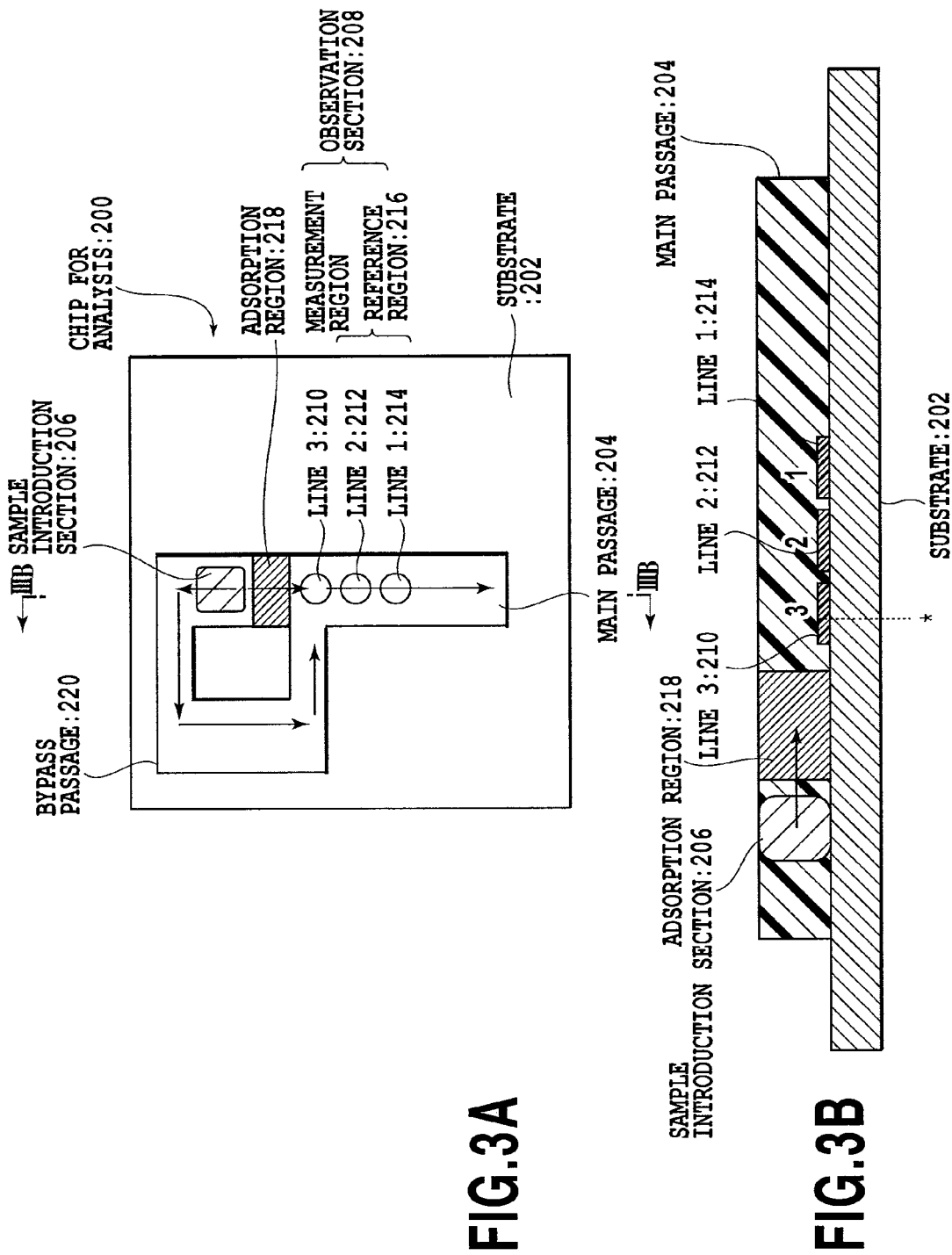
FIG. 3A is a planar schematic diagram showing a chip for optical analysis of another embodiment of the present invention.
FIG. 3B is a cross-sectional schematic diagram showing the chip for optical analysis of another embodiment of the present invention.

The chip for optical analysis 200 corresponding to the second embodiment of the present invention will be explained with reference to FIGS. 3A and 3B. FIG. 3A is a planar view of the chip for optical analysis of the second embodiment, and FIG. 3B is a cross-sectional view of FIG. 3A at IIIB-IIIB. As shown in FIGS. 3A and 3B, the chip for optical analysis of the second embodiment comprises a main passage 204 similar to the one explained in FIGS. 2A and 2B on a substrate 202. The main passage is provided with a sample introduction section 206 at one end thereof for delivering a sample by drops. Furthermore, the main passage is provided with an observation section 208 comprising lines 1 to 3 (214, 212, 210). The observation section 208 comprises a reference region 216 comprising lines 1 and 2 (214, 212) and a measurement region for detecting a substance to be measured (210 in FIGS. 3A and 3B). The main passage is further provided with an adsorption region 218 for selectively adsorbing the substance to be measured between the sample introduction section and the observation section. FIGS. 3A and 3B show an example of the reference region provided with lines of two types, but the reference region may be provided with a line of one type. Features such as structures of the main passage, the substrate, the adsorption region, and the observation section, materials, and the like are as explained in the first embodiment.

Figure 8:
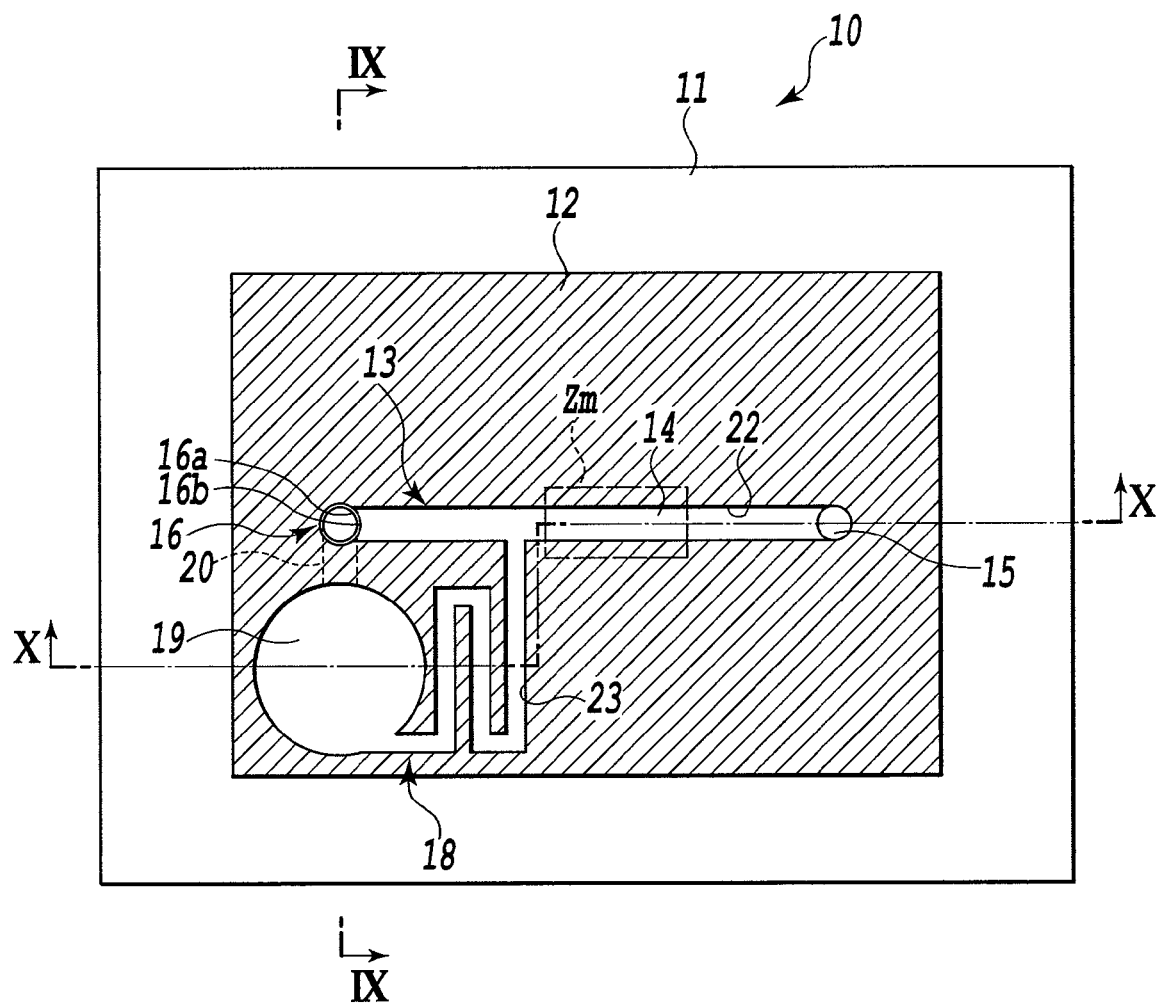
FIG. 8 is a cross-sectional schematic diagram showing a chip for optical analysis of one embodiment of the present invention.

The chip for optical analysis of the second embodiment comprises a bypass passage 220 that bypasses the adsorption region from the sample introduction section to the observation section. The bypass passage is composed of a porous membrane and is positioned so that a sample passed through the bypass passage should reach the observation section taking more time than a sample passed through the adsorption region. So long as this condition is satisfied, the shape, the material, and the like of the bypass passage are not limited. For example, the bypass passage may be rectangular as shown in FIGS. 3A and 3B or ladder-like as shown in FIG. 8 described later. In the chip for optical analysis of the present invention, porous membranes forming the main passage and the bypass passage are preferably of the same material.

In the chip for optical analysis of the present invention, the passage composed of a porous membrane has a thickness of 300 to 10,000 nm (10 µm), preferably 300 to 1000 nm. Furthermore, the full-length of the passage, the positions of the measurement region and the reference region on the substrate, and the like can be suitably selected to suite the optical measurement method (for example, a surface plasmon resonance measurement method), and such selection can be easily made by those skilled in the art.

The operation of the chip for optical analysis of the second embodiment will be explained below. After a liquid sample containing a substance to be measured is introduced into the chip for optical analysis from the sample introduction section, the liquid sample are allowed to flow in the main passage direction and the bypass passage direction due to capillary phenomenon of the porous material.

The liquid sample flowing in the main passage direction first reaches the adsorption region in which an adsorbent exists. Since an adsorbent that adsorbs the substance to be measured is contained in the adsorption region, the substance to be measured is adsorbed, and other substances are allowed to flow to the observation region. Here, since the liquid sample flowing to the observation region does not contain the substance to be measured, it means that a reference sample reaches the observation region.

Meanwhile, since the liquid sample flowing in the bypass passage direction directly reaches the observation section without passing through the adsorption region, it still contains the substance to be measured. Furthermore, since the liquid sample flowing via the bypass passage reaches the observation section taking more time than the sample passed through the adsorption region (sample flowing via the main passage), it reaches the observation section later than the reference sample which flows via the main passage and in which the substance to be measured is free reaches the observation section.

Thus, the liquid sample flowing via the main passage serves as a reference sample, and the liquid sample flowing via the bypass passage serves as a measurement sample. Since a time lag is generated between the liquid samples flowing via the main passage and the bypass passage to reach the observation section, the reference sample and the substance to be measured can be measured by introducing a sample once.

A method for manufacturing the chip for optical analysis of the present invention will be explained with reference to the drawings.

Figure 4:
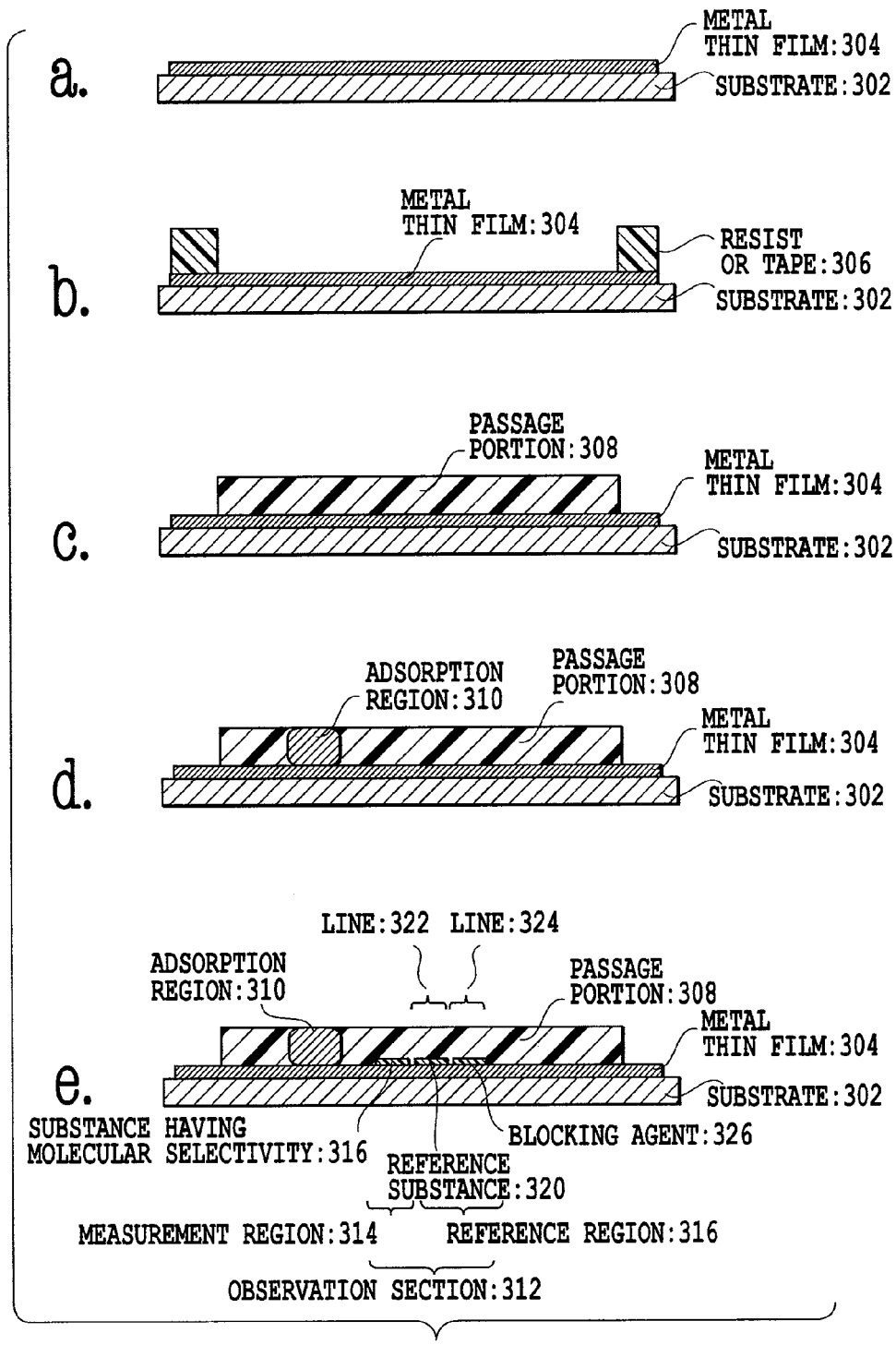
FIGS. 4(a) to (e) show manufacturing processes of the chip for optical analysis of the present invention.

First, a metal thin film 304 such as gold or the like is formed on a substrate 302 by vapor-deposition or the like (FIG. 4 (a)). The metal thin film has a membrane thickness of about 50 nm when used for, for example, a surface plasmon resonance (SPR) device. Subsequently, a pattern is formed with a resist or a tape 306 on the metal thin film, so that the passage shape should be exposed (FIG. 4 (b)). In the case of a chip for optical analysis having such a bypass passage 220 as shown in FIGS. 3A and 3B, a pattern including a bypass passage can be formed. Subsequently, an organic solvent solution of a cellulose derivative such as cellulose acetate is applied by a spin coat method or the like and dried to remove the organic solvent, and the resist or the tape is removed to form a passage portion 308 (FIG. 4 (c)).

Subsequently, a solution containing an adsorbent that adsorbs a substance to be measured is applied to a portion corresponding to the adsorption region 310 of the passage to immobilize the adsorbent on the passage (FIG. 4 (d)). When the adsorbent is applied, a portion corresponding to the adsorption region may be activated, if necessary. For example, when protein A is used as an adsorbent, it is preferable to apply an aqueous carbodiimide solution to the adsorption region beforehand to activate a porous material.

Subsequently, a substance having molecular selectivity and a reference substance are immobilized on a portion corresponding to the observation section of the passage. The substance having molecular selectivity can be immobilized by adding dropwise a solution containing the substance having molecular selectivity 316 on to the measurement region 314 of the observation section 312 and drying the solution. The reference substance can be immobilized by adding dropwise a solution containing a reference substance 320 that does not bind to the substance to be measured but is similar to the substance having molecular selectivity onto the reference region 318 of the observation section and drying the solution (FIG. 4 (e)). When the reference region is provided with two lines 322, 324 as shown in FIGS. 2A and 2B, a reference region neither containing a substance having molecular selectivity nor a reference substance may be formed by immobilizing the reference substance on one of these lines as described above and adding dropwise a solution containing a blocking agent 326 onto the other and drying the solution. When the blocking agent is added dropwise onto the measurement region and the reference region containing the reference substance to block these regions, it is preferable to provide a region containing a blocking agent, so that the measurement conditions should be uniform.

Another method for manufacturing the chip for optical analysis of the present invention will be explained.

As described above, a metal thin film 304 is formed on a substrate 302, and a pattern is formed on the metal thin film with a resist or a tape 306, which pattern has the passage shape that exposes the metal thin film. At this time, a portion corresponding to the adsorption region 310 of the passage is not exposed the metal thin film (FIG. 5 (a)). Furthermore, when such a bypass passage 220 as shown in FIG. 3 is formed, a pattern including a bypass passage can be formed. Subsequently, an organic solvent solution of a cellulose derivative such as cellulose acetate is applied by a spin coat method or the like and dried to remove the organic solvent, and the resist or the tape is removed to form a passage portion 402 separated by the adsorption region (FIG. 5 (b)).

Figure 5:
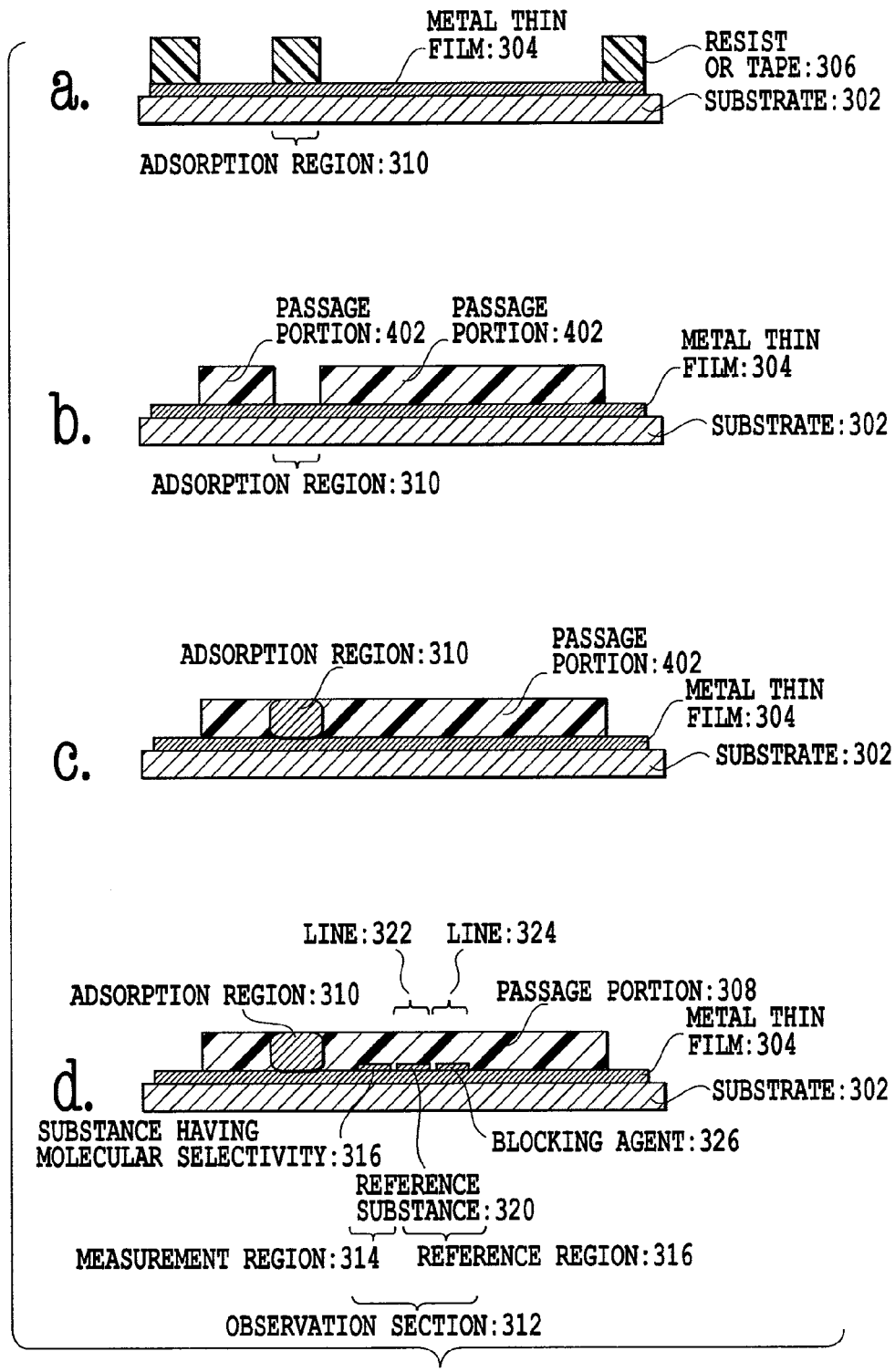
FIGS. 5(a) to (d) show manufacturing processes of the chip for optical analysis of the present invention.

Subsequently, a solution containing an adsorbent that adsorbs a substance to be measured (preferably, a solution mixed with a porous material for forming the passage) is applied to the adsorption region 310, the solvent or the like is removed, and an adsorption region is formed so as to connect to the passage portion 402 (FIG. 5 (c)). Subsequently, the observation section is formed as described above, and thus a chip for optical analysis in which the passage 308 is formed can be manufactured (FIG. 5 (*d*)).

In the present specification, "immobilization" encompasses chemical or physical binding onto the passage including the case where an adsorbent, a substance having molecular selectivity, a reference substance, and the like are adsorbed to the passage as described above.

In the above explanation of the first and second embodiments, an example where a porous membrane is used for the passage, and the sample moves by capillary phenomenon has been shown, but the present invention is not limited to this example. For example, sucking-up means such as a pump can be provided at a portion downstream of the passage without using a porous membrane for the passage. Furthermore, the above-mentioned aspects (1) and (3) of the present invention are combined in the above-described first embodiment, and the above-mentioned aspects (2) (an adsorption region is provided) and (3) of the present invention are combined in the second embodiment, but the present invention is not limited to these embodiments. A chip for optical analysis can be constituted by the above-mentioned aspect (1) of the present invention solely, or the above-mentioned aspect (2) of the present invention solely. In these cases, the chip can be constituted so that a target substance can be suitably measured at the observation section.

A chip for optical analysis 10 of another embodiment (third embodiment) used for the surface plasmon resonance measurement device 1 will be explained. This chip for optical analysis corresponds to a combination of the above-mentioned aspects (2) (an adsorption region is provided) and (3) of the present invention.

Figure 9:
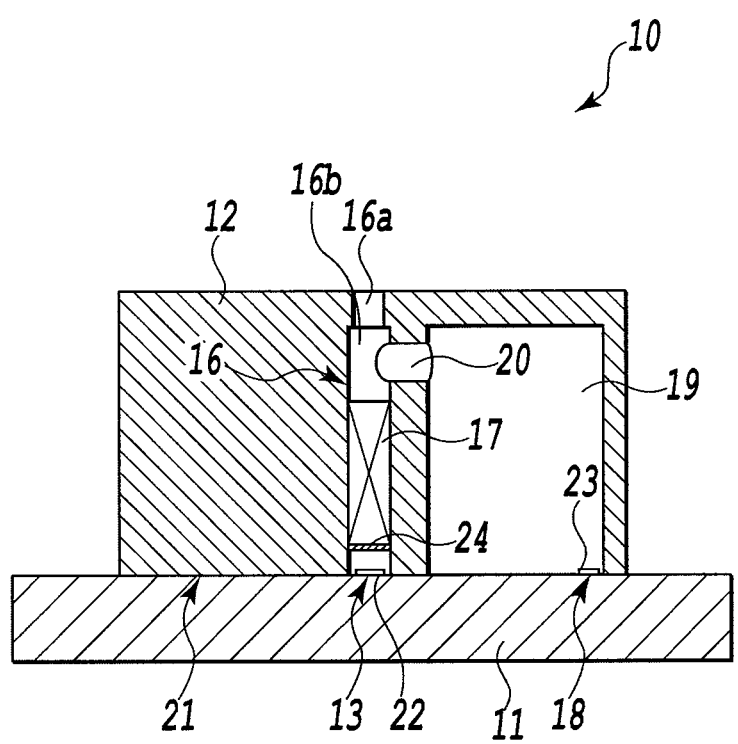
FIG. 9 is a sagittal section view at IX-IX in FIG. 8.
Figure 10:
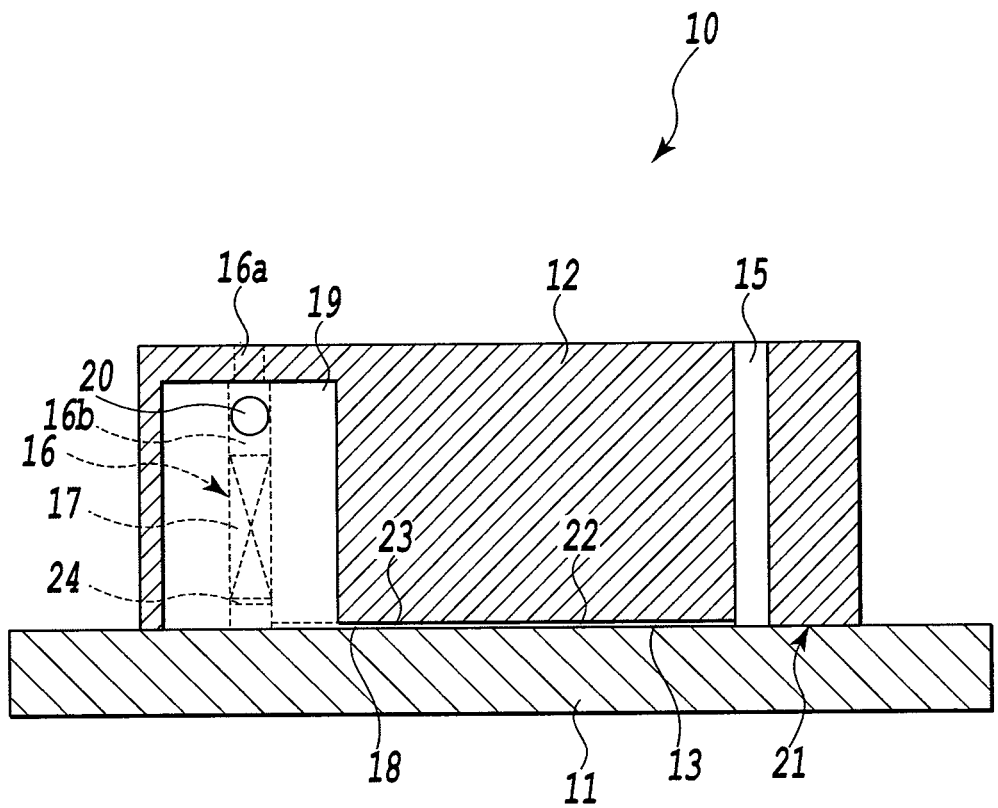
FIG. 10 is a sagittal section view at X-X in FIG. 8.

The cross-sectional structure of the chip for optical analysis 10 is shown in FIG. 8. The sagittal section structure thereof at IX-IX and the sagittal section structure thereof at X-X are shown in FIGS. 9 and 10, respectively. The chip for optical analysis 10 in this embodiment has a substrate 11 and a chip main body 12 joined to a surface of the substrate 11. The substrate 11 in this embodiment is a thin plate having, for example, a length of 10 mm, a width of 16 mm, and a height of 1 mm and is made of glass or plastic transparent to a measurement light Lm. Furthermore, the chip main body 12 in this embodiment is a rectangular solid shape having, for example, a length of 7 mm, a width of 10 mm, and a height of 4 mm, and a resin that can be easily machined, etched, or the like is used. Polydimethylsiloxane (PDMS) processed into a predetermined shape is used in this embodiment.

Figure 11:
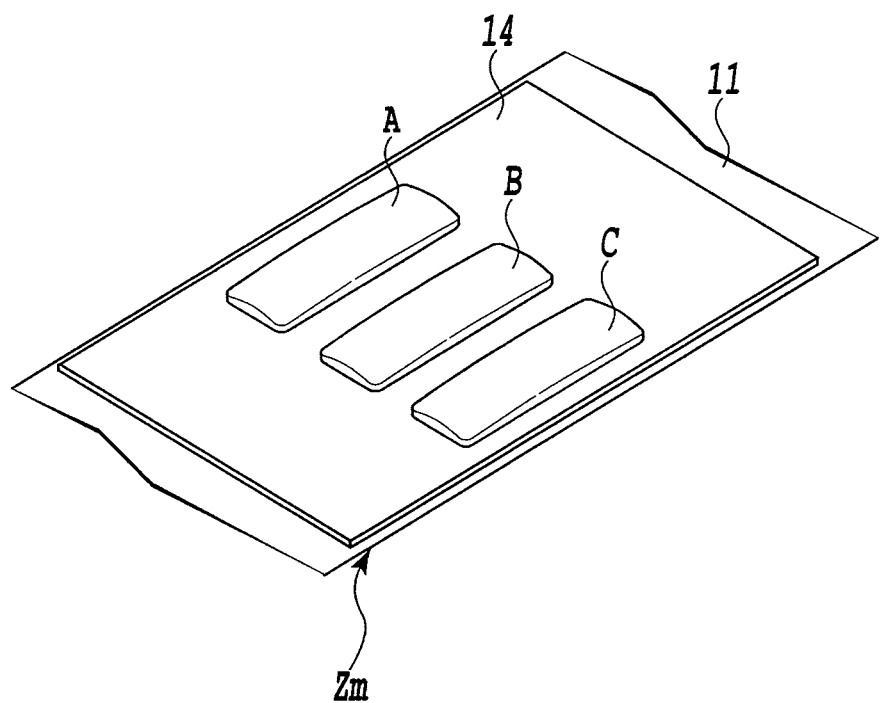
FIG. 11 is an extracted and enlarged stereoscopic three-dimensional view transparently showing a part of a measurement region of the chip for optical analysis shown in FIG. 8.

A gold thin film layer 14 (see FIG. 11) with a rectangular pattern having a thickness of about 50 nm facing a first passage 13 positioned at the observation section Zm surrounded by a two-dot chain line in FIG. 8 when the chip main body 12 is joined can be formed on a surface of the substrate 11 by vapor-deposition or the like. It is preferable to provide the observation section Zm virtually at the center of the substrate 11. An appearance of this gold thin film layer 14 portion is enlarged and shown in FIG. 11. An antibody as a material having molecular selectivity is immobilized on the observation section on the gold thin film layer 14 to form antibody-immobilized regions A, B, and C. In this embodiment, three antibody-immobilized regions A, B, and C can be formed so as to cross the first passage 13 by limiting the amount of a liquid containing an antibody added dropwise onto the gold thin film layer 14. These three antibody-immobilized regions A, B, and C in this embodiment can contain anti-human IgG, anti-rabbit IgG, and anti-goat IgG, which have selectivity to different antigens. These antibody-immobilized regions A, B, and C can be formed by adding dropwise liquids containing the corresponding antibodies onto the predetermined antibody-immobilized regions A, B, and C on the gold thin film layer 14 and allowing to stand for a predetermined time, then sucking the remaining liquids, and attaching a part of antibodies contained in the liquids onto a surface of the gold thin film layer 14.

Meanwhile, a through hole 15 of about 0.6 mm serving as a discharge port is formed at the center in the width direction (vertical direction in FIG. 8) on one end side in the longitudinal direction of the chip main body 12 (horizontal direction in FIG. 8). Furthermore, a stepped hole 16 forming a part of the first passage 13 is formed at the center in the width direction on the other end side in the longitudinal direction of the chip main body 12. The inside diameter of a small-diameter portion 16a of the stepped hole 16 serving as an introduction port is, for example, about 0.45 mm, and the inside diameter of a large-diameter portion 16b filled with a filter 17 described later is, for example, 0.6 mm. Furthermore, a blind hole 19 having an inside diameter of, for example, 2.5 mm serving as a liquid collecting section of the second passage 18 is formed adjacent to this stepped hole 16 at one corner on the other end side in the longitudinal direction of the chip main body 12. The bottom part of this blind hole 19 and the large-diameter portion 16b of the stepped hole 16 are communicated with each other via a continuous hole 20 which is a part of the second passage 18. Specifically, the connection section of the continuous hole 20 and the large-diameter portion 16b of the stepped hole 16 serves as a branching section in the present invention. In this embodiment, since the diameter of the blind hole 19 is set very large as compared with the diameter and the length of the continuous hole 20, the continuous hole 20 can be formed by inserting into the blind hole 19 a drill head for drilling the continuous hole 20 from this blind hole 19. Formation methods other than this method can be used, but the number of processing processes may be increased, or an additional process for preventing a liquid spill may be required. A groove 22 in a straight line having a width of, for example, 0.5 mm and a depth, that is, a height of, for example, 50 μm that is communicated with the through hole 15 and the large-diameter portion 16b of the stepped hole 16 as a part of the first passage 13, and a ladder-like groove 23 having, for example, a width of 0.3 mm and a height of 50 μm that is communicated with the halfway of this groove 22 on one end side thereof and communicate with the blind hole 19 as a part of the second passage 18 on the other end side are carved in the joint surface 21 with the substrate 11 of this chip main body 12. The connection section with the groove 22 that is in a straight line with an end of this ladder-like groove 23 is a merging section of the two passages 13, 18, and the first passage 13 positioned at the center in the longitudinal direction of the groove 22 in a straight line downstream thereof serves as an observation section Zm. A spiral or maze-like groove can be formed instead of the ladder-like groove 23, and these shapes, cross-sectional structures, and the like are basically arbitrarily selected.

A filter 17 for capturing a predetermined component contained in a liquid to be measured (also referred to as an adsorbent in the present specification) is filled on the downstream side where the side is the connection section of the stepped hole 16 with the continuous hole 20 in the large-diameter portion 16b of the stepped hole 16 in the first passage 13. As the filter 17 in this embodiment, gel-like microparticles using active carbon, molecular sieve, dextran, cellulose, agarose, or curdlan as the main material, silica modified with an organic matter containing a hydrophobic group, alumina microparticles, or the like can be used. This filter 17 is held by a porous holding member 24 made of glass fiber injected into the large-diameter portion 16b of the stepped hole 16 at the central portion of the large-diameter portion 16b of the stepped hole 16, so that the inlet portion of the continuous hole 20 should not be blocked.

Plasma treatment is performed on the joint surface 21 of the chip main body 12 formed as described above, the joint surface 21 of the chip main body 12 and the surface of the substrate 11 are overlapped and pressed to each other, so that a gold thin film layer 14 formed on the surface of the substrate 11 should be positioned at a predetermined position of the groove 22 in a straight line, that is, the observation section Zm, and the joint surface 21 of the chip main body 12 is joined to the surface of the substrate 11 in an integrated fashion. Thus, the first passage 13 reaching the groove 22 that forms a straight line from the small-diameter portion 16a of the stepped hole 16 via the large-diameter portion 16b and the second passage 18 reaching the ladder-like groove 23 from the continuous hole 20 through the blind hole 19 are formed to prepare a chip for optical analysis 10. It is noted that, so long as the volume of the first passage 13 is sufficiently smaller than that of the second passage 18, these passages 13, 18 may have any form, which is not limited to the embodiments described above.

Figure 12:
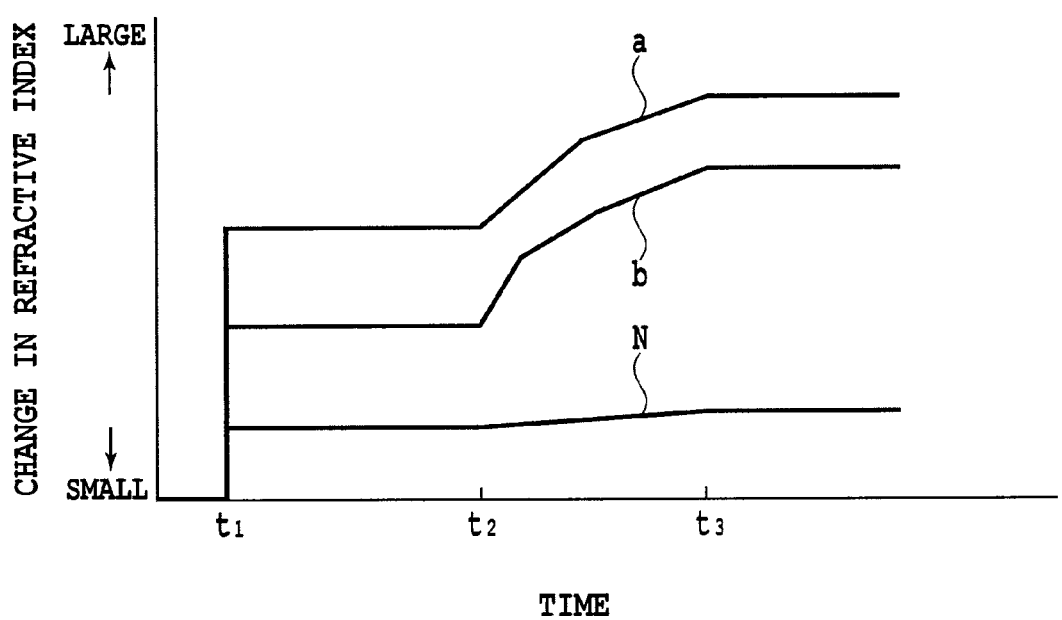
FIG. 12 is a schematic graph showing measurement results using the chip for optical analysis shown in FIG. 8 as changes in current values.

When measurement is performed using the surface plasmon resonance measurement device shown in FIG. 1, a tube for supplying a liquid to be measured (not shown) is connected to the introduction port of the chip for optical analysis 10, specifically the small-diameter portion 16a of the stepped hole 16, and a phosphate buffer having a concentration of 0.1 mol/L containing antigens which are measurement objects, specifically human IgG (sample a) and rabbit IgG (sample b), and albumin as a liquid to be measured, which is an impurity, is supplied into the chip for optical analysis 10 using a micro syringe pump (not shown). Then, the liquid that has been measured and passed through the observation section Zm is discharged out of the chip for optical analysis 10 using a discharge port, specifically a waste fluid tube (not shown) connected to the through hole 15. Meanwhile, a measurement light from the light source 2 is irradiated on the observation section Zm from the substrate 11 of the chip for optical analysis 10, a reflected light thereof Lr guided to the light detector 4 is processed at the signal processing section, and the refractive index and changes in the refractive index are obtained. These measurement results are shown in FIG. 12.

The liquid to be measured is passed through the filter 17 from the first passage 13. Meanwhile, the antigens and albumin, which are an impurity, are adsorbed to the filter 17 so as to be used as a reference sample, and the liquid reaches the observation section Zm of the first passage 13 at the time of $t_1$. A signal of the surface plasmon resonance angle detected here, specifically a refractive index N serves as the measurement reference. Subsequently, the liquid to be measured containing the impurity and the antigens from the second passage 18 is allowed to flow from the merging section of the first passage 13 into the first passage 13 and reaches the observation section Zm at the time of $t_2$, which is later than $t_1$, and the mixing ratio thereof becomes stable after $t_3$. Here, the impurity and the antigens which are the measurement objects in the liquid to be measured are adsorbed to the antibody-immobilized regions A, B, and C of the observation section. Albumin as an impurity is equally adsorbed to all the three antibody-immobilized regions A, B, and C, but human IgG and rabbit IgG, antigens, are selectively adsorbed to the corresponding antibody-immobilized regions A and B, respectively. As a result, differences between the antibody-immobilized region C, on which anti-goat IgG is immobilized, and other two antibody-immobilized regions A and B are detected as changes in the refractive indices a and b corresponding to signals by human IgG and rabbit IgG. In an antigen-antibody reaction in a surface modification format using a total reflection-type optical system, the reaction rate is proportional to the antigen concentration, and human IgG in the liquid to be measured can be quantified from changes over time of the surface plasmon resonance angle. That is, human IgG and rabbit IgG can be quantified from changes over time in the surface plasmon resonance angles represented as changes in the refractive indices a and b.

In the case of a liquid to be measured containing many impurities that are hardly passed through the filter 17 incorporated in the first passage 13 or a liquid to be measured with high viscosity, a greater difference needs to be generated in time $t_1$, $t_2$ to reach the observation section Zm from the branching section through the first and second passages 13, 18. To this end, a hydrophilically treated layer may be formed on the wall surface of the second passage 18. For example, a silane coupling agent having an amino group can be applied on the inner peripheral wall of the ladder-like groove 23 of the above-described embodiments and the surface of the substrate 11 forming the second passage 18 together therewith to form a hydrophilically treated layer. Since a hydrophilic silane coupling material has an action of drawing the water content in a phosphate buffer in the second passage 18 in contact therewith, the flow of the phosphate buffer in the second passage 18 is suppressed, time $t_2$ to reach the observation section Zm is further increased.

Figure 13:
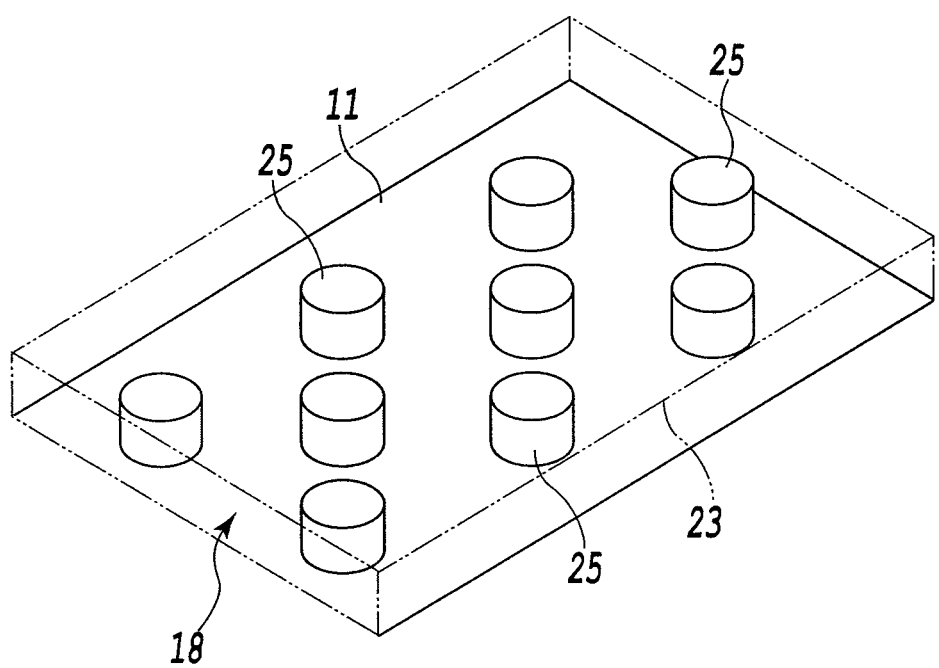
FIG. 13 is an extracted and enlarged stereoscopic three-dimensional view transparently showing a part of a second passage in the chip for optical analysis of another embodiment of the present invention.

Similarly, as means for generating a great difference in time $t_1$, $t_2$ to reach the observation section Zm from the branching section through the first and second passages 13, 18, it is also effective to form one or more passage resistance-increasing blocks 25 protruded from the surface of the substrate 11 facing the second passage 18 into the second passage 18, as shown in FIG. 13, at a predetermined interval or randomly. The passage resistance-increasing block 25 in this embodiment constitutes a cylinder having, for example, a diameter of 50 μm and a height of 30 μm and is formed as a pattern on the surface of the substrate 11 using a resist. Thus, the resistance of the second passage 18 can be increased by allowing the passage resistance-increasing block 25 to exist in the second passage 18, and time to reach the observation section Zm can be increased.

In the above-described third embodiment, the liquid that has been measured is discharged out of the chip for optical analysis 10 from the discharge port, specifically the through hole 15, but it can be held in the chip for optical analysis 10.

Figure 14:
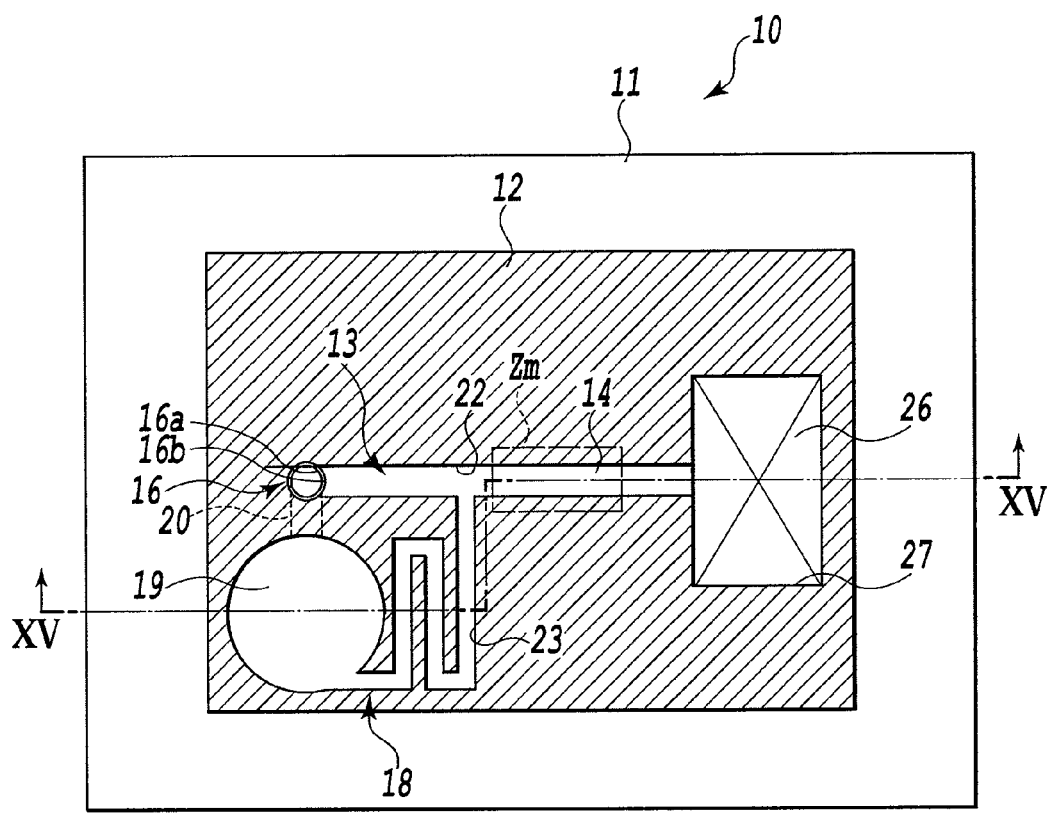
FIG. 14 is a cross-sectional view showing a chip for optical analysis of another embodiment of the present invention.
Figure 15:
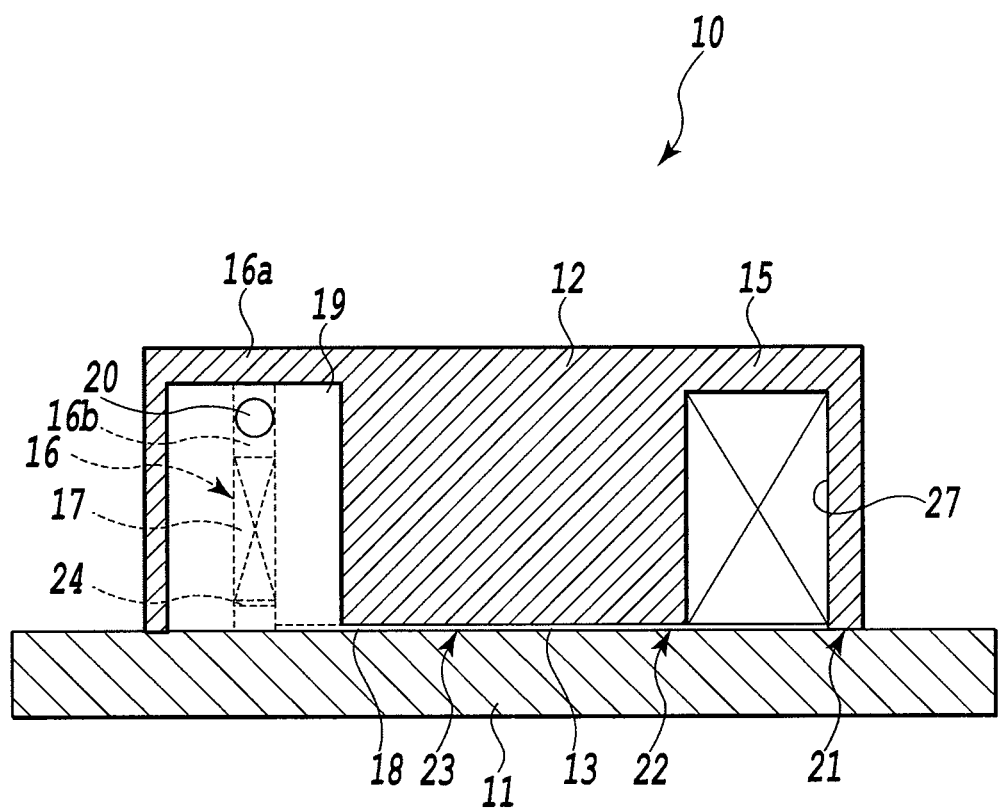
FIG. 15 is a sagittal section view at XV-XV shown in FIG. 14.

An example of the chip for optical analysis 10 in such a modified form is shown in FIGS. 14 and 15. FIG. 14 shows a cross-sectional structure, and FIG. 15 shows sagittal section structure at XV-XV in FIG. 14. In these figures, components having the same function as in the above-described embodiments are only labeled with the same symbols, and the same explanation will be omitted. In this embodiment, instead of the above-described through hole 15, a void portion 27 housing an absorption body 26 is formed in the chip main body 12 so as to connect to an end of the first passage 13. An absorption body 26 such as a pulp or a gelated polymer is housed for absorbing and holding a liquid in this void portion 27. In this embodiment, since the absorption body 26 absorbs and holds the measured fluid when the measured fluid reaches the absorption body 26 in the void portion 27 from the first passage 13, the measured fluid introduced into the chip for optical analysis 10 from an introduction port, specifically the small-diameter portion 16a of the stepped hole 16, can be automatically sucked, and the measured fluid can also be led from the second passage 18 to the absorption body 26 without operating a measured fluid supplying pump.

In the chip for optical analysis of the third embodiment, the passage may be a narrow tube, but otherwise the passage can be formed with a porous material. Examples of the porous material include those explained in the first and second embodiments. Furthermore, the third embodiment shows an example of a combination of the above-mentioned aspects (2) (adsorption region is provided) and (3) of the present invention, but the scope of the present invention is not limited to this example. The chip for optical analysis can be constituted by the above-mentioned aspect (2) of the present invention solely. In this case, it is sufficient to constitute the chip for optical analysis, so that a target substance can be suitably measured at the observation section.

Since the chip for optical analysis according to the above-described third embodiment is provided with means for allowing a liquid to be measured to reach the observation section from the branching section through the first passage earlier than reaching the observation section from the branching section through the second passage, it has the following effects in addition to the above-described effects.

When there is provided a liquid absorption holding section which is incorporated in the chip main body and is connected to the first passage on the downstream side of the observation section for absorbing a liquid to be measured passed through the observation section, an electric-powered pump for allowing the liquid to be measured to flow into the chip for optical analysis or the like can be omitted. Furthermore, since the waste fluid after measurement is held in the liquid absorption holding section and is not allowed to flow out, post-treatment becomes easy.

When a hydrophilically treated layer is formed on the wall surface of the second passage, the flow of a liquid to be measured in the second passage is suppressed since the water component in the liquid to be measured passed through the second passage has affinity with the hydrophilically treated layer. As a result, the liquid to be measured can reach the observation section from the branching section through the first passage earlier than reaching the observation section from the branching section through the second passage.

When at least one passage resistance-increasing block protruded into the second passage from the surface of the substrate facing the second passage is formed, the passage resistance-increasing block suppresses the flow of the liquid to be measured in the second passage. As a result, the liquid to be measured can reach the observation section from the branching section through the first passage earlier than reaching the observation section from the branching section through the second passage.

When the volume of the first passage reaching the merging section from the branching section is set larger than that of the second passage, the liquid to be measured can reach the observation section from the branching section through the first passage earlier than reaching the observation section from the branching section through the second passage. In particular, when a liquid collecting section for collecting the liquid to be measured is positioned in the middle of the second passage, a reference sample reaching the observation section through the filter and a fluid to be measured reaching the observation section through the second passage can reach the observation section with a great time lag.

When a material having molecular selectivity such as an antibody or an antigen is immobilized on the observation section of the first passage, an immune reaction related to an organism can be measured. In particular, when the material having molecular selectivity is an enzyme, detection of a biologically-relevant substance or a drug, quality control of food, or detection of an environmentally acting substance is enabled. In the case of an oligonucleoside or a ribonucleoside, information of a substance to be measured at a gene level can be identified. In the case of a modified cyclodextrin compound, an ion or an amino acid can be selectively measured. Furthermore, when the filter contains a dextran gel using protein A as a modifier, a reference sample in which an IgG-type immunity substance is free can be prepared in this chip for optical analysis, and a chip for optical analysis for measuring an IgG-type immunity substance can be obtained. When at least one of organic membrane-coated silica and organic membrane-coated alumina is contained, a reference sample which proteins other than IgG, amino acids, and ions are free can be prepared in the chip for optical analysis, and a chip for optical analysis for detecting proteins other than IgG, amino acids, and ions can be obtained. When a measurement object contains various kinds of impurities, the chip for optical analysis can be used by filling a dextran gel using protein A as a modifier at the bottom and organic membrane-coated silica or organic membrane-coated alumina at the top.

The fourth and fifth embodiments of the present invention will be explained. The fourth and fifth embodiments correspond to the above-mentioned aspect (3) of the present invention.

The chip for optical analysis of the fourth embodiment comprises a substrate, a metal thin film on the substrate, and an observation section on the metal thin film, wherein the observation section is provided with a measurement region and a reference region. In the chip for optical analysis, on the measurement region, a first substance having molecular selectivity that selectively interacts with a specific molecule is immobilized, and on the reference region, a second substance having molecular selectivity that is different only in selectivity to the specific molecule with which the first substance having molecular selectivity interacts and is comparable to the first substance having molecular selectivity in other characteristics is immobilized, and preferably, the first substance having molecular selectivity and the second substance having molecular selectivity are immobilized on the substrate by the same method.

The chip for optical analysis of the fourth embodiment of the present invention will be explained with reference to the drawings.

Figure 16A:
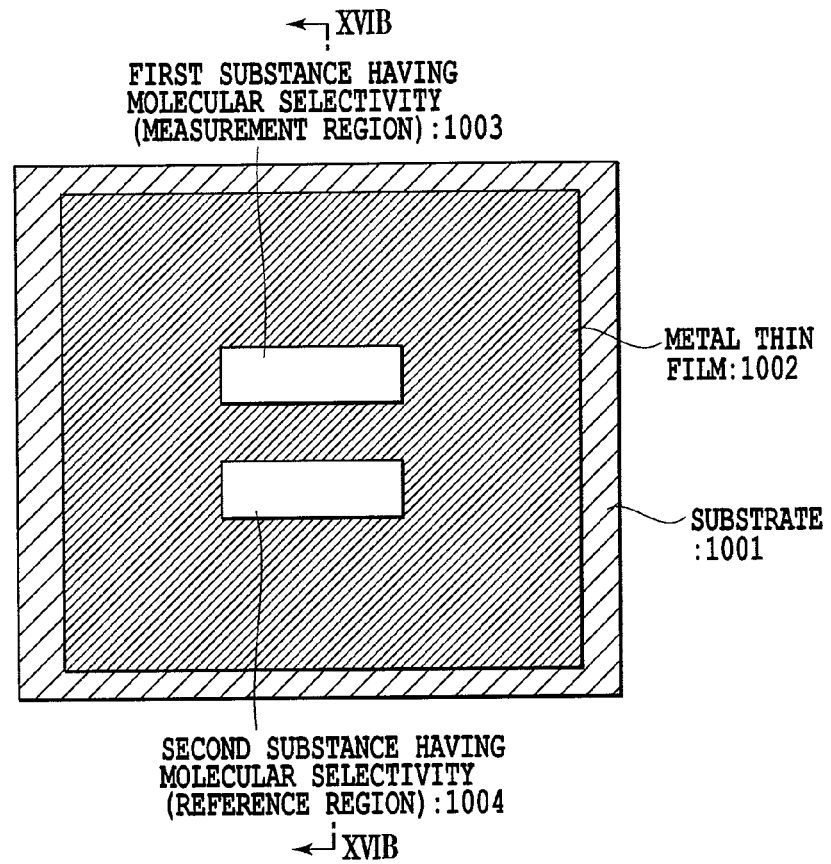
FIG. 16A is a planar schematic diagram showing a chip for optical analysis of one embodiment of the present invention.
Figure 16B:
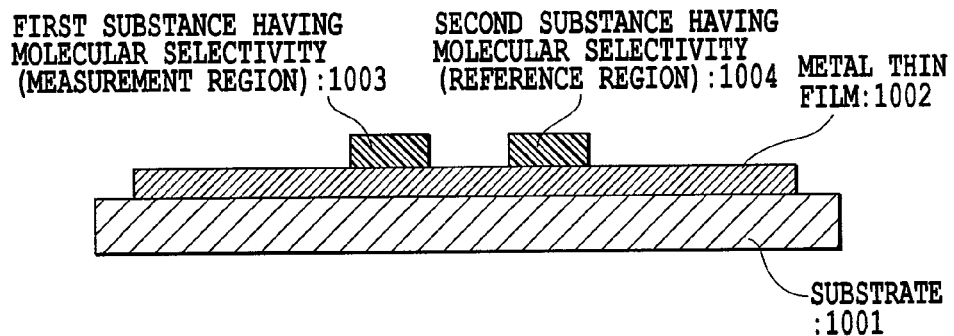
FIG. 16B is a cross-sectional schematic diagram showing a chip for optical analysis of one embodiment of the present invention.

The chip for optical analysis of the fourth embodiment of the present invention is as shown in FIGS. 16A and 16B. FIG. 16B is a cross-sectional view at XVIB-XVIB of FIG. 16A. This chip for optical analysis has a metal thin film 1002, preferably a gold thin film, formed on a substrate 1001 by a method such as vapor-deposition, and a measurement region 1003 and a reference region 1004 are provided on this gold thin film. The measurement region 1003 and the reference region 1004 are preferably arranged in parallel in a straight line as shown in the figure.

The measurement region and the reference region are arranged along a passage of a flow cell for transporting a sample as described later, but either the measurement region or the reference region may be arranged closer to the inlet side of the flow cell.

Examples of the substances having molecular selectivity used in the measurement region and the reference region include biologically-relevant substances such as antibodies, antigens, enzymes, DNA, RNA, and proteins, nonbiologically-relevant substances such as ionophores and modified products of dextran, and so forth. Furthermore, antibodies obtained by protein engineering that have different selectivity and similar three-dimensional structures and the like can also be used for both regions.

It is preferable to design the substances having molecular selectivity used in the measurement region and the reference region, so that they should be different from a substance to be measured only in selectivity. Such a design includes synthesis of the substance having molecular selectivity so as to be different from a substance to be measured only in selectivity (any chemical or biological means) and inactivation of the substance having molecular selectivity so as to be different from a substance to be measured only in selectivity.

Specifically, a first substance having molecular selectivity that selectively interacts with a substance to be measured in the chip for optical analysis is immobilized on the measurement region. The first substance having molecular selectivity can selectively interact with the substance to be measured, and specific examples thereof include such biologically-relevant substances and nonbiologically-relevant substances mentioned above, those obtained by protein engineering techniques, and so forth.

A second substance having molecular selectivity is immobilized on the reference region. The second substance having molecular selectivity is not particularly limited so long as it is different only in selectivity to a specific molecule with which the first substance having molecular selectivity interacts and is comparable to the first substance having molecular selectivity in other characteristics. That is, the second substance having molecular selectivity is a substance that is comparable to the first substance having molecular selectivity in characteristics, except that it does not interact with molecules other than the substance to be measured. In the present invention, it is preferable to use a substance of the same type or kind as that of the first substance having molecular selectivity as the second substance having molecular selectivity.

As the second substance having molecular selectivity, for example, a substance obtained by inactivating the first substance having molecular selectivity can be used. Here, "inactivation" means subjecting the first substance having molecular selectivity to a specific processing, so that only selectivity to a substance to be measured should be different from that of the first substance having molecular selectivity. Examples of such an inactivation processing include irradiation with a high energy ray such as an X-ray, a gamma($\gamma$)-ray, or an electron beam, heat treatment, electrochemical oxidation or reduction, contact with an acidic or alkaline buffer, and so forth.

Not only the second substance having molecular selectivity can be obtained by the above-described methods, but also when the first substance having molecular selectivity is an antibody, an anti-antibody of the same kinds can be used as the second substance having molecular selectivity. For example, the case where antibody C having selectivity to a substance to be measured c is immobilized on the measurement region is illustrated. At this time, an anti-antibody (antibody C') prepared by administering a substance different from the substance to be measured c to the same animal from which the antibody C has been obtained as an antigen (for example, a bovine, a goat, a rabbit, a mouse, a rat, a sheep, a dog, a feline, an equine, camel, etc.) is immobilized on the reference region. When antibody C is IgG, IgA, IgM, IgE, IgD, or the like, antibody C' is anti-IgG, anti-IgA, anti-IgM, anti-IgE, anti-IgD, or the like, respectively. Whether these anti-antibodies bind to Fc or Fab of these anti-antibodies is the same, and these anti-antibodies are different only in selectivity to the substance to be measured.

Furthermore, considering the case where antigen D having selectivity to a substance to be measured d is used as the first substance having molecular selectivity (that is, antigen D is immobilized on the measurement region), antigen D', which is different from the antigen D only in selectivity to the substance to be measured d, can be used as the second substance having molecular selectivity to be immobilized on the reference region.

Furthermore, DNA, RNA, a protein, or the like can be used as the first substance having molecular selectivity. These are not particularly limited so long as they can achieve a selective coupling with the substance to be measured, such as formation of a conjugate.

When DNA or RNA is used as the first substance having molecular selectivity, the second substance having molecular selectivity can be obtained by adding, replacing, deleting, or the like several nucleotides constituting the first substance having molecular selectivity. Specifically, when DNA is used as the first substance having molecular selectivity, it is preferable to obtain the second substance having molecular selectivity by replacing 10% or less of nucleotides constituting the first substance having molecular selectivity.

The substrate is not particularly limited so long as it is made of a material that is transparent to a light used in a measurement device on which the chip for optical analysis is mounted (for example, a surface plasmon resonance [SPR] device), and any material can be used. For example, a glass substrate, a plastic substrate, or the like can be used.

When a biologically-relevant substance such as an antibody is used in the measurement region in the present invention, effects on the reaction rate itself of an interaction between the biologically-relevant substance and the substance to be measured, for example, an antigen-antibody reaction are minimal even when many impurities exist in the sample solution, since selectivity of a biologically-relevant substance is very high. Therefore, even when many impurities exist in the sample solution, the substance to be measured can be detected and/or quantified with high sensitivity and high precision.

In the present specification, interaction means a chemical or physical action of a substance having molecular selectivity with a substance to be measured, and examples thereof include a hydrogen bond, an ionic bond, an intermolecular bond, uptake of a substance into a molecule, formation of a conjugate, adsorption, and so forth. For example, when the above-mentioned biologically-relevant substance is used, an antigen-antibody reaction, an enzyme-substrate interaction, a base pair bonding in formation of a double strand of DNA or RNA, and so forth can be mentioned.

Figure 17:
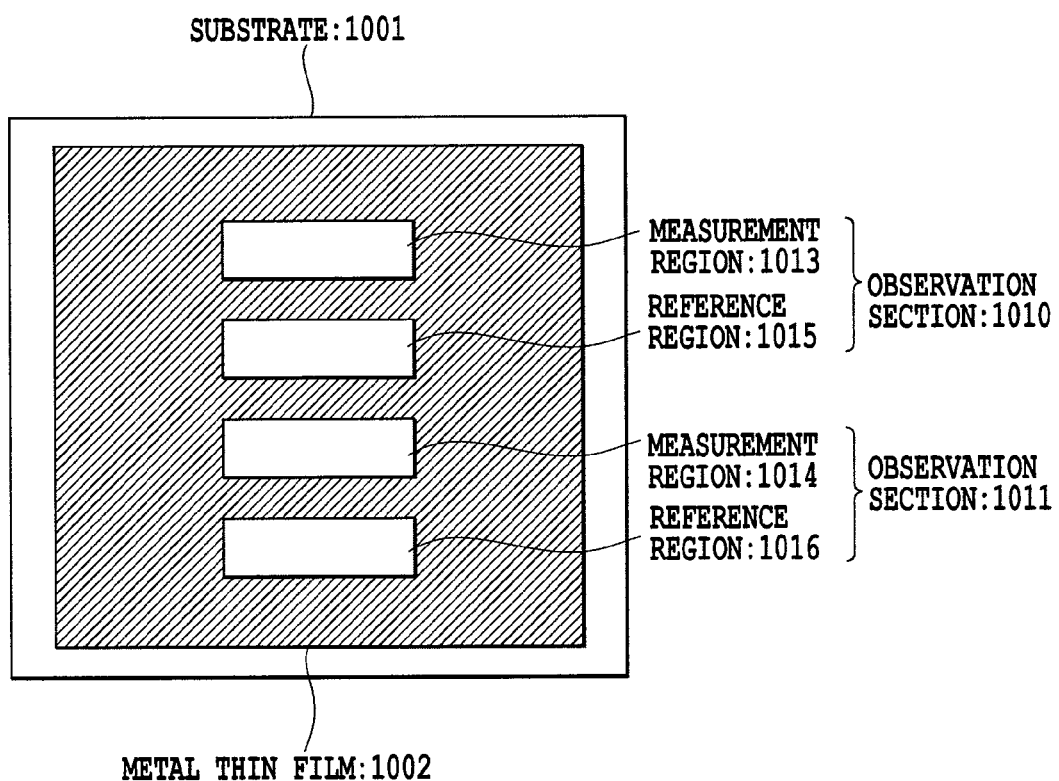
FIG. 17 is a schematic diagram showing a chip for optical analysis of another embodiment of the present invention.

The fifth embodiment of the present invention will be explained. The chip for optical analysis of the fifth embodiment is as shown in FIG. 17. This chip for optical analysis has a metal thin film 1002, preferably a gold thin film, formed on a substrate 1001 by a method such as vapor-deposition. A plurality of measurement regions 1013, 1015 and reference regions 1014, 1016 are provided in parallel on this gold thin film. In this embodiment, the measurement region 1013 and the reference region 1015 and the measurement region 1014 and the reference region 1016 as sets constitute observation sections 1010 and 1011. In the observation section 1010 and the observation section 1011, first substances having molecular selectivity of different types are immobilized on the respective measurement regions, so that different types of molecules can be detected. Furthermore, the second substance having molecular selectivity is immobilized in accordance with the first substance having molecular selectivity. The first substance having molecular selectivity and the second substance having molecular selectivity are as described above. This embodiment shows an example where two observation sections are provided, but the present invention is not limited to this example, and even more observation sections may be provided.

When a plurality of observation sections are provided on the substrate, it is preferable to arrange each observation section along a passage of a flow cell for transporting a sample, preferably, so that observation sections are aligned in parallel in a straight line.

Positions of the measurement region and the reference region on the substrate and the like in the chip for optical analysis of the present invention can be suitably selected to suit the optical measurement method (for example, a surface plasmon resonance measurement method). Such a selection can be suitably made by those skilled in the art.

As described above, in the chip for optical analysis of the present invention, effects of adsorption or accumulation of impurities is offset by applying the first substance having molecular selectivity to the measurement region and the second substance having molecular selectivity different from the first substance having molecular selectivity only in selectivity to the substance to be measured to the reference region, and a change in the baseline for measurement can be minimized when a sample is measured.

A method for manufacturing the chips for optical analysis of the fourth embodiment and the fifth embodiment will be explained with reference to the drawings.

Figure 18:
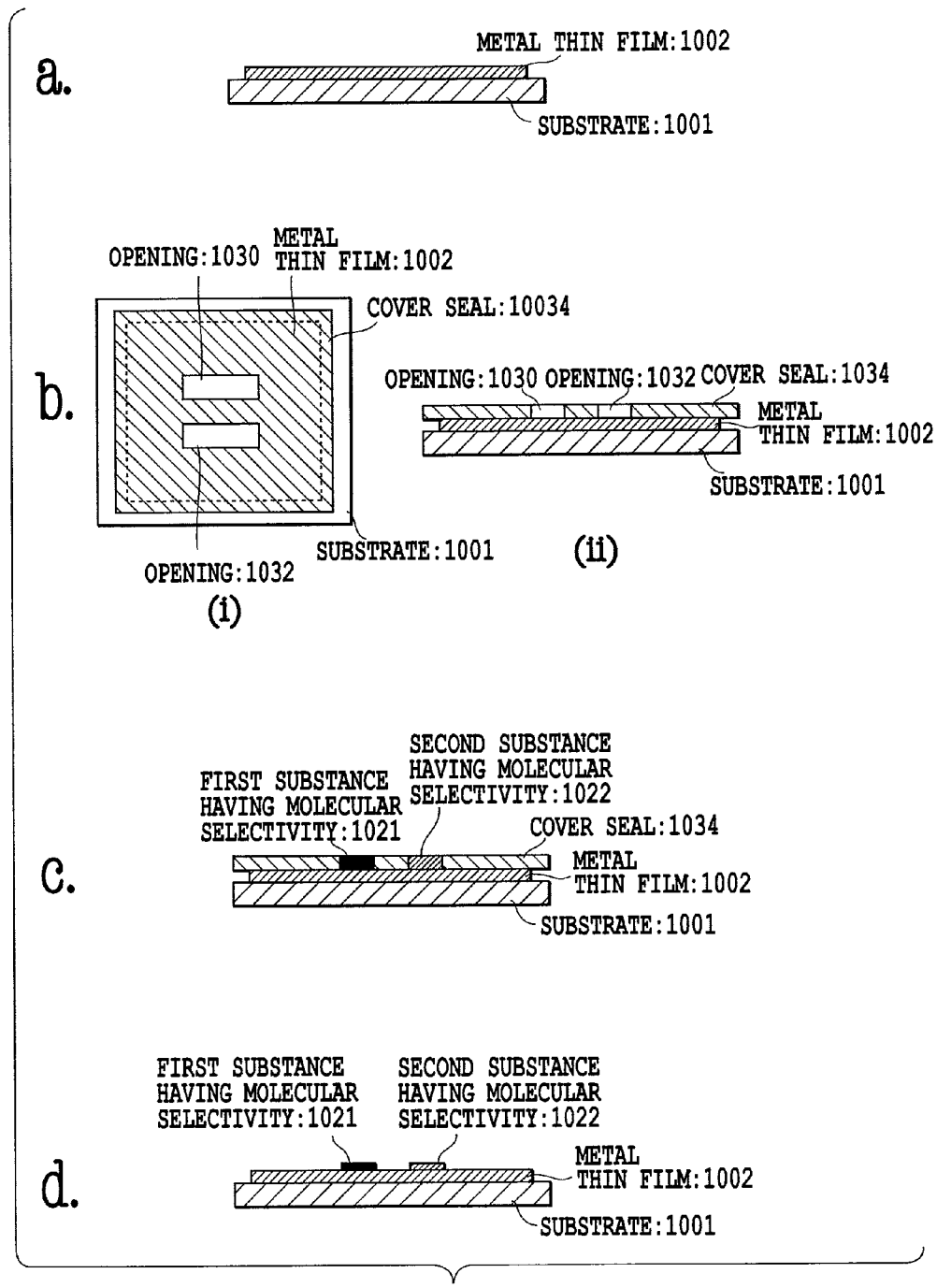
FIGS. 18(a) to (d) are views for explaining manufacturing processes of the chip for optical analysis shown in FIG. 16.

The chip for optical analysis of the fourth embodiment can be prepared by, for example, the procedures shown in FIGS. 18 (*a*) to (*d*). First, a metal thin film 1002 of gold or the like is formed on a substrate 1001 by vapor-deposition or the like (FIG. 18 (*a*)). The metal thin film has a membrane thickness of about 50 nm, for example, when used for an SPR device. Subsequently, a cover seal 1034 having openings 1030, 1032 corresponding to the measurement region 1003 and the reference region 1004 are attached on the metal thin film (FIG. 18 (*b*) (i) and (ii)). Solutions 1021, 1022 each containing the first substance having molecular selectivity or the second substance having molecular selectivity (for example, a phosphate buffer solution of an antibody or an anti-antibody) are added dropwise into these openings, respectively, and allowed to stand for a predetermined time (FIG. 18 (*c*)). Then, the solutions are removed, and the cover seal is peeled off to obtain a chip for optical analysis in which the first substance having molecular selectivity and the second substance having molecular selectivity are immobilized on the measurement region and the reference region (FIG. 18 (*d*)), respectively. The predetermined time for the standing varies depending on the immobilized material, but, for example, is several minutes to 60 min, preferably about 20 min when a phosphate buffer solution of an antibody is used. In the present invention, "immobilization" encompasses a chemical or physical binding with the top of a substrate or a metal thin film including the placement of the first substance having molecular selectivity and the second substance having molecular selectivity on the substrate, preferably a metal thin film as described above.

The chip for optical analysis of the fifth embodiment can be prepared by using a cover seal provided with openings corresponding to a plurality of observation sections shown in FIG. 18 (*b*) and immobilizing a substance having molecular selectivity depending on the substance to be measured on each observation section.

Another method for manufacturing a chip for optical analysis having one observation section will be explained with reference to FIGS. 19 and 20. First, a substrate 1001 is covered with a mask 1040. This mask has three openings opened in portions forming a metal thin film 1048, 1049, 1050, openings corresponding to pad sections 1044, 1045, and openings corresponding to joining sections 1046, 1047 connecting the metal thin film 1049 and the pad section 1045 and the metal thin film 1050 and the pad section 1044. Metal thin films 1048, 1049, 1050 made of a material such as gold (FIG. 19 (*a*)) is formed through these openings by means such as vapor-deposition.

Subsequently, the mask is removed, a cover seal 1054 having openings 1051, 1052 is attached on portions of the metal thin films 1048, 1049, and a solution of the first substance having molecular selectivity 1055 is added dropwise into these openings 1051, 1052 and left stand for a predetermined time (FIG. 19 *b*)). Then, the solution is removed, and the cover seal is peeled off to obtain a substrate in which the first substance having molecular selectivity 1055 is immobilized on the metal thin films 1048, 1049 (FIG. 19 (*c*)).

Figure 19:
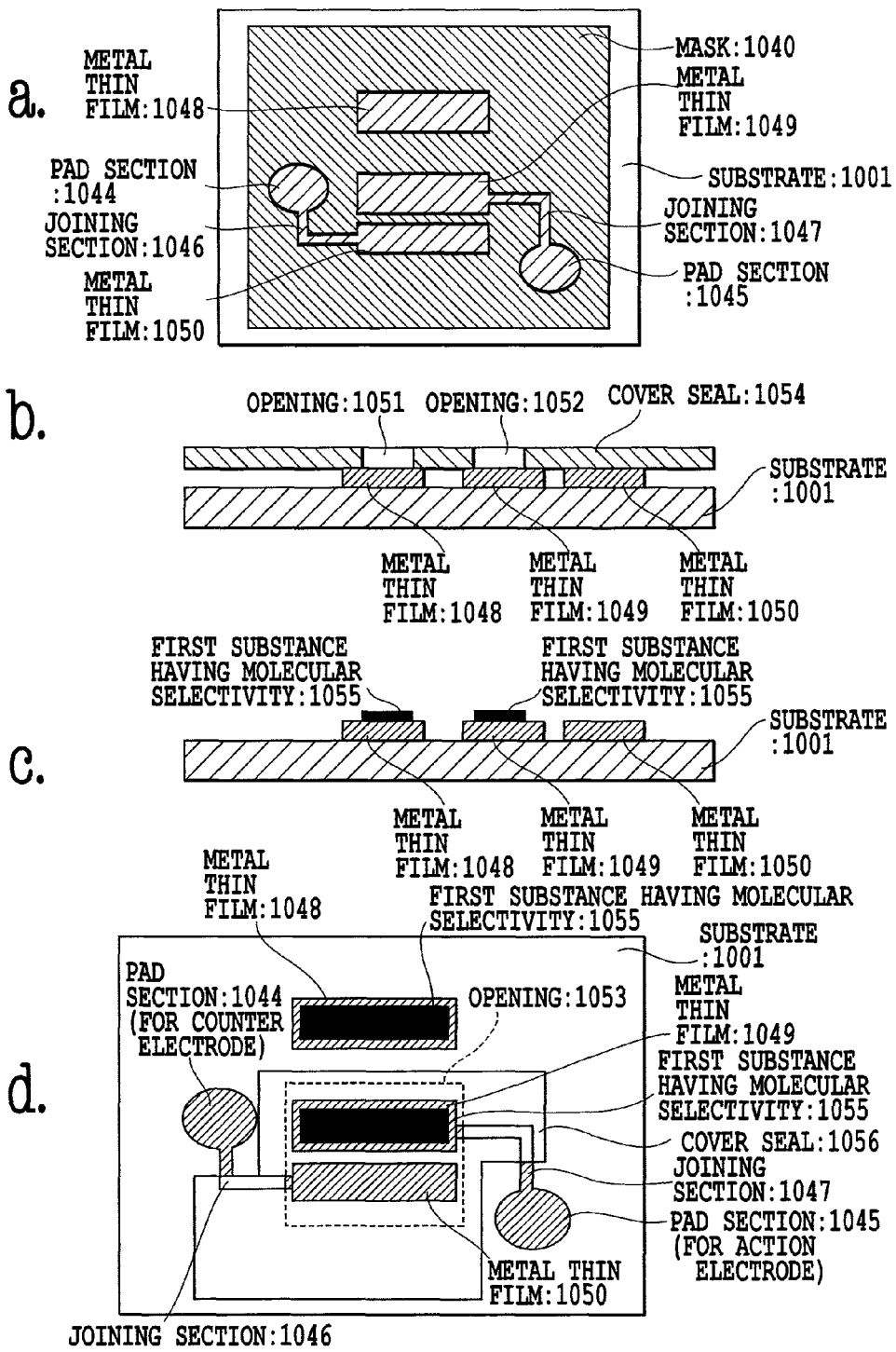
FIGS. 19(a) to (d) are views for explaining other manufacturing processes of the chip for optical analysis corresponding to FIG. 16.
Figure 20A:
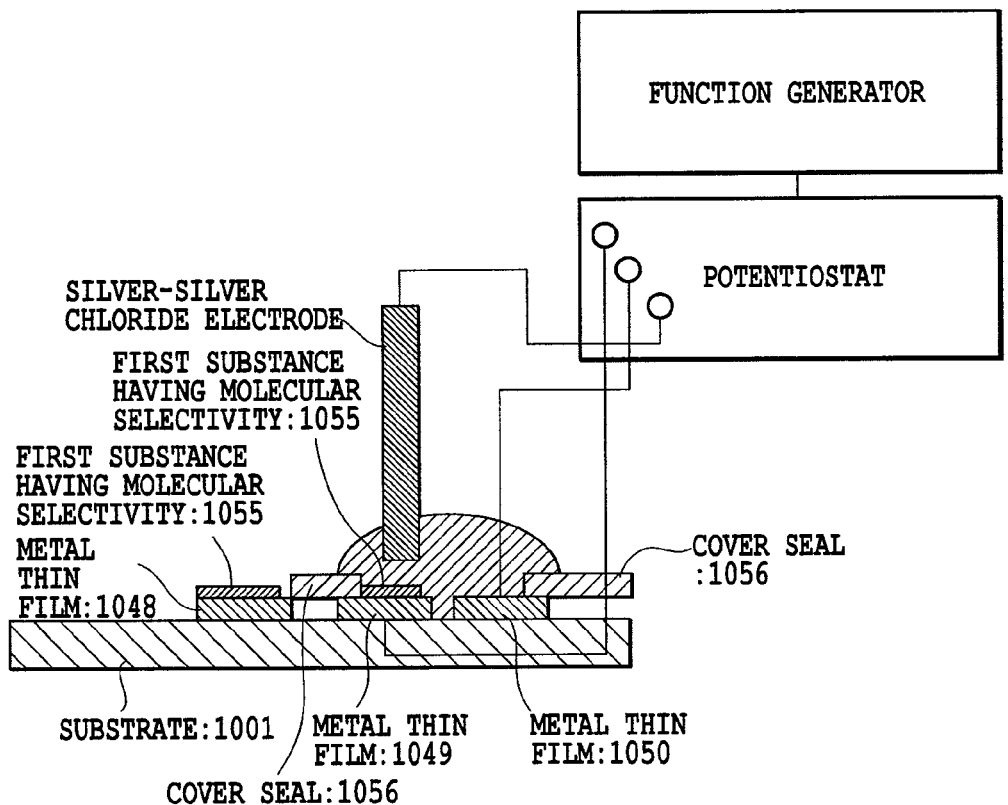
FIG. 20A is a schematic diagram showing an electrochemical device used for inactivation of a substance having molecular selectivity in a reference region in FIG. 19.
Figure 20B:
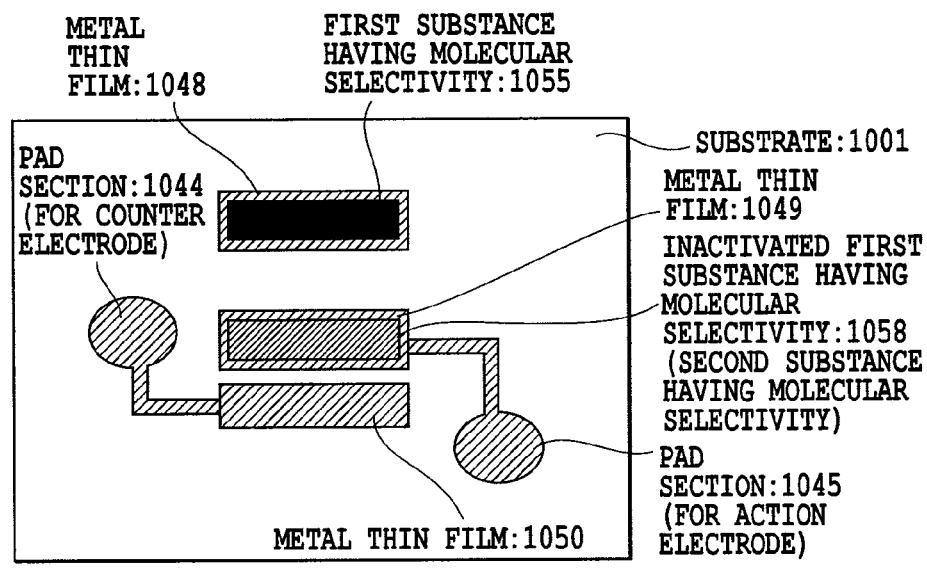
FIG. 20B is a schematic diagram showing the chip for optical analysis of the present invention.

Subsequently, as shown in FIG. 19 (*d*), a cover seal 1056 having a pattern of an opening 1053 with which a part of the joining sections 1046, 1047 is covered and portions of the metal thin films 1049, 1050 are well-shaped is attached. This well-shaped opening 1053 can hold an electrolyte solution. An electrolyte solution (for example, a phosphate buffer solution) is added dropwise into the above-mentioned well 1053 of the substrate thus obtained, and the first substance having molecular selectivity on the metal thin film 1049 is inactivated using a silver-silver chloride reference electrode, a potentiostat, and a function generator as shown in FIG. 20A and used as the second substance having molecular selectivity 1058. Finally, the reference electrode, the electrolyte solution, the cover seal, the potentiostat, the function generator, and the like are removed to obtain the chip for optical analysis (FIG. 20B).

In the method for manufacturing the chip for optical analysis of the present invention, when the second substance having molecular selectivity is prepared by inactivating the first substance having molecular selectivity, the first substance having molecular selectivity may be inactivated after the first substance having molecular selectivity is immobilized on the reference region beforehand. Alternatively, the first substance having molecular selectivity is inactivated beforehand, and then the inactivated first substance having molecular selectivity may be immobilized on the reference region.

Figure 21:
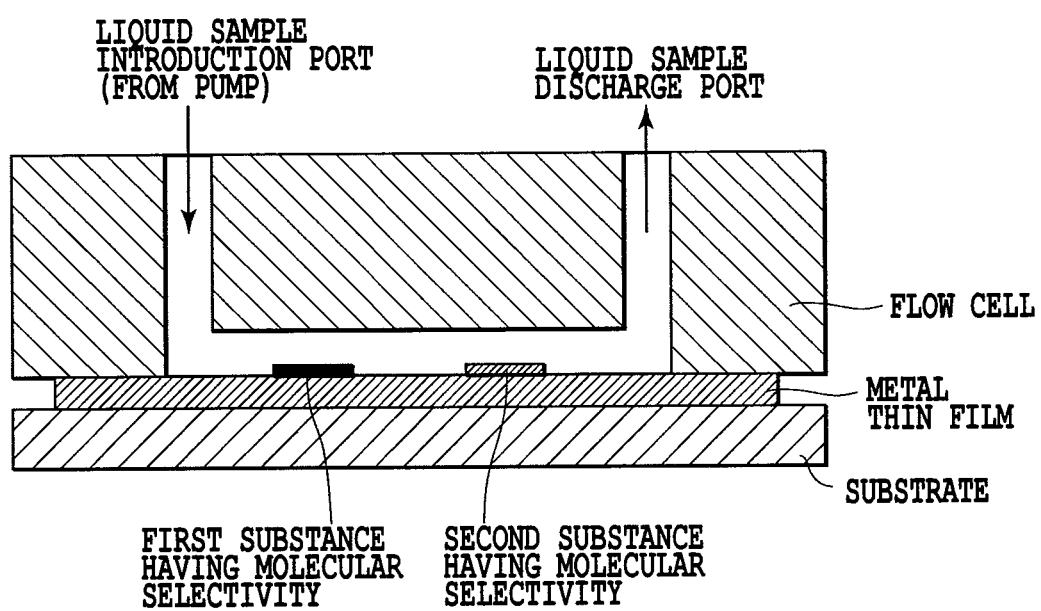
FIG. 21 is a schematic diagram of a case where a flow cell is provided in the chip for optical analysis.

The chip for optical analysis thus obtained is mounted on, for example, a surface plasmon resonance device (for example, the device described in Patent Document 1), is equipped with a flow cell made of polydimethylsiloxane (PDMS) at the top as shown in FIG. 21, and then is used. A liquid sample can be introduced into the flow cell from the micro syringe pump via a tube.

When a liquid sample is introduced, a sample solution containing impurities flows into the measurement region and the reference region at the same time, and impurities are adsorbed or accumulated in the measurement region and the reference region at the same time. As a result, when a difference between the measurement region and the reference region is measured, effects of adsorption and accumulation of impurities are offset, and a change in the baseline for measurement can be minimized. Therefore, since a change in the baseline can be minimized as compared with a signal obtained upon detection of a substance to be measured at a low concentration in the liquid sample, a substance to be measured can be detected or quantified with high sensitivity and high precision.

The fourth and fifth embodiments correspond to the above-mentioned aspect (3) of the present invention. However, the present invention is not limited to these embodiments, and the above-mentioned aspect (1) and/or (2) and the above-mentioned aspect (3) can be used in combination.

The chip for optical analysis of the present invention can be applied to total reflection optical systems and assay systems used by immobilizing a substance having molecular selectivity and can be applied as a chip for measurement of absorption based on not only the surface plasmon resonance measurement methods but also total reflection measurement methods utilizing a prism or a diffraction grating.

EXAMPLES

The present invention will be explained more specifically with reference to the following examples.

Example 1

This example shows a chip for optical analysis for a passage without a bypass passage as shown in FIGS. 2A and 2B, for which a protein A adsorbent is used as an adsorbent.

Cellulose acetate was dissolved in an organic solvent to prepare a cellulose acetate solution. A gold thin film (thickness 50 nm) was formed on a BK7 glass substrate by vapor-deposition. A resist membrane or a tape was applied onto this gold thin film, and a pattern in which a portion of the gold thin film corresponding to a passage was exposed was formed. The patterned gold/glass substrate was mounted on a spin coater, the cellulose acetate solution prepared beforehand was added dropwise to the substrate, then the substrate was rotated, and the organic solvent was evaporated to form a white membrane-form passage. Subsequently, a buffer solution of protein A was prepared and added dropwise to an adsorption region of the passage, and protein A was adsorbed to the passage to form the adsorption region. The region to which protein A was adsorbed had been activated beforehand by adding dropwise an aqueous solution of carbodiimide and drying the solution. Thus, a passage having a length of 10 mm, a width of 1 mm, and a thickness of 1 μm was formed.

Subsequently, a small amount of a phosphate buffer solution containing 100 μg·mL$^{-1}$ anti-human IgG (0.1 M, pH 6.8) was added dropwise onto a portion of the passage corresponding to a measurement region (a portion corresponding to line 3 in FIGS. 2A and 2B) and dried to immobilize the antibody. Similarly, a phosphate buffer solution containing 100 μg·mL$^{-1}$ anti-goat IgG was added dropwise onto a portion adjacent to the region on which anti-human IgG was immobilized (a portion corresponding to line 2 in FIGS. 2A and 2B) and dried to immobilize a reference antibody.

Subsequently, a phosphate buffer solution containing 4 mg·mL$^{-1}$ bovine serum albumin was prepared as a blocking agent solution, and this solution was added dropwise onto the measurement region and the reference region on which the antibodies were immobilized (lines 3 and 2 in FIGS. 2A and 2B) and further another region in the reference region (a portion corresponding to line 1 in FIGS. 2A and 2B) and dried.

Figure 6:
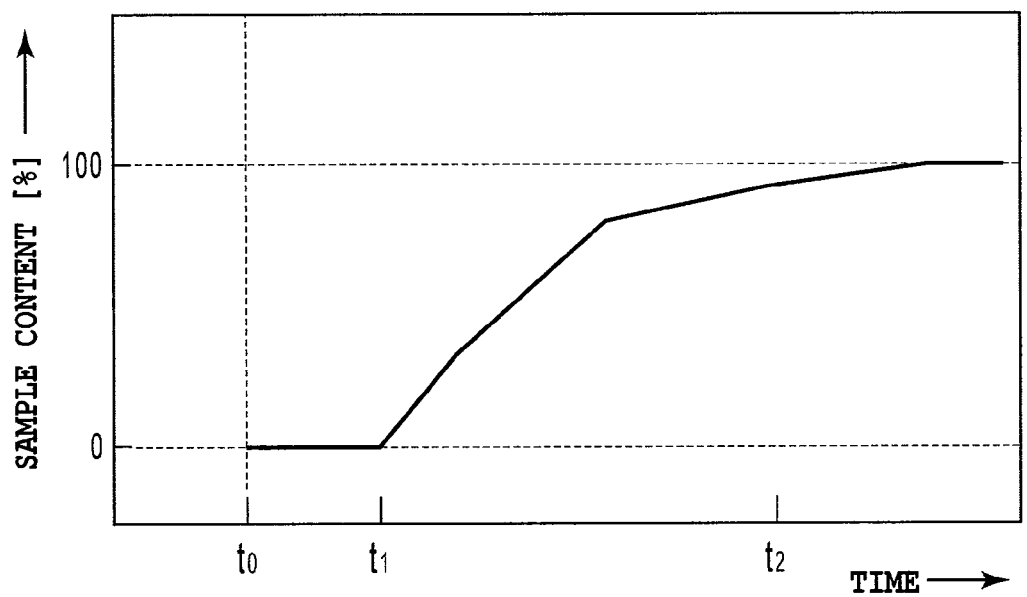
FIG. 6 shows changes over time of a substance to be measured in a solution that reached the position of * on a passage.

The prepared chip for optical analysis was mounted on a prism of a surface plasmon resonance measurement device via a matching oil. A phosphate buffer solution containing human IgG was added dropwise onto a sample introduction section of the passage of the chip for optical analysis as a liquid sample. Human IgG that is a substance to be measured in the liquid sample is adsorbed to protein A in the adsorption region, the phosphate buffer solution not containing human IgG reaches to the observation region, and SPR is observed. FIG. 6 shows profiles of the concentration of human IgG in the liquid sample which reaches the portion represented by in FIG. 2B. As shown in FIG. 6, the reference sample not containing human IgG reaches the measurement region at the time of t0. The angle of SPR observed from time t0 to time t1, at which the liquid sample containing human IgG reaches the measurement region, serves as a base level for measurement.

Figure 7:
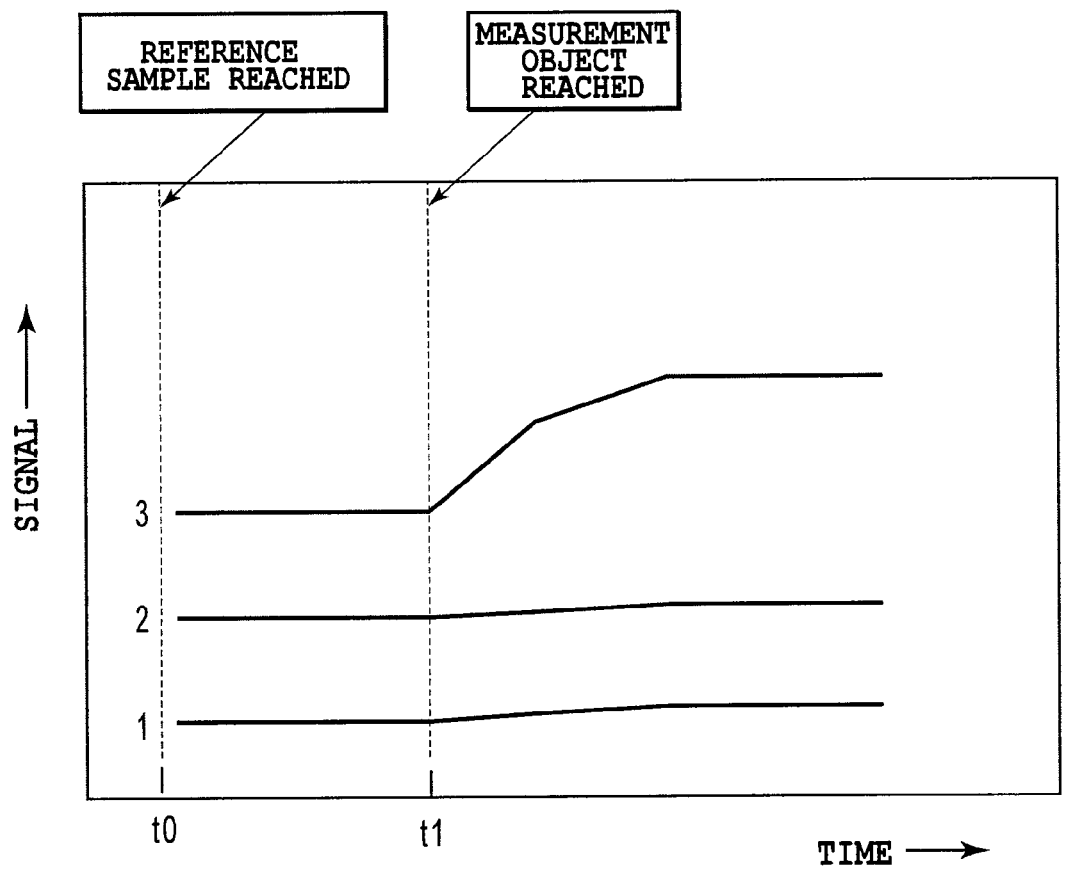
FIG. 7 shows changes over time in intensity of a signal measured at the positions of lines 1 to 3.

Subsequently, after the adsorbent region is saturated by the liquid sample is further added dropwise, or substance to be measured is prevented from being adsorbed to the adsorbent by protecting (or covered) the adsorption region with a plastic or the like, a large volume of the liquid sample is introduced through the sample introduction section, and thus the liquid sample containing human IgG reaches the measurement region, and human IgG binds selectively to the anti-human IgG in the measurement region. On the other hand, neither of the region on which the anti-goat IgG was immobilized and the region on which only a blocking agent was immobilized in the reference region binds to human IgG. Therefore, at this stage, the angle of SPR increases only in the measurement region (a portion corresponding to line 3 in FIGS. 2A and 2B), and the angle of SPR only slightly increases in the reference region (lines 2 and 1 in FIGS. 2A and 2B) as shown in FIG. 7. The difference between the measurement region (line 3) and the region on which anti-goat IgG was immobilized (line 2) in the reference region represents selective binding of human IgG to anti-human IgG, and human IgG can be quantified from these changes over time in the increase in the angles.

Since the protein A adsorbent has a property of selectively coupling to the Fc region of IgG, this example is suitable for preparation of a reference sample by removing only IgG from a sample.

Example 2

This example shows a chip for optical analysis for a passage without a bypass passage as shown in FIGS. 2A and 2B, for which a modified dextran microparticle adsorbent is used as an adsorbent.

A cellulose acetate solution obtained by dissolving cellulose acetate in an organic solvent and modified dextran microparticles (obtained from the microparticlation of methacrylate-modified dextran by radical polymerization) (diameter 15 to 30 μm) were mixed to prepare a cellulose acetate-dextran microparticle mixture solution. A gold thin film (thickness 50 nm) was formed on a BK7 glass substrate by vapor-deposition. A resist membrane or a tape was applied onto this gold thin film to form a pattern in which a portion of the gold thin film corresponding to a passage was exposed. At this time, an adsorption region of the passage on the metal thin film was prevented from being exposed, and the cellulose acetate solution was prevented from being deposited on the adsorption region. Subsequently, the patterned gold/glass substrate was mounted on a spin coater, the previously prepared cellulose acetate solution was added dropwise, then the substrate was rotated, and the organic solvent was evaporated to form a white membrane-form passage. Subsequently, the previously prepared cellulose acetate-dextran microparticle mixture solution was added dropwise onto the adsorption region and dried, and the adsorption region was formed so as to connect to the previously formed white membrane-form passage. Thus, a passage having a length of 10 mm, a width of 1 mm, and a thickness of 1 μm was formed.

Subsequently, a small amount of a phosphate buffer solution containing 100 μg·mL$^{-1}$ anti-human IgG (0.1 M, pH 6.8) was added dropwise onto a portion of the passage corresponding to a measurement region (a portion corresponding to line 3 in FIGS. 2A and 2B) and dried to immobilize the antibody. Similarly, a phosphate buffer solution containing 100 μg·mL$^{-1}$ anti-goat IgG was added dropwise onto a portion adjacent to the region on which anti-human IgG was immobilized (a portion corresponding to line 2 in FIGS. 2A and 2B) and dried to immobilize a reference antibody.

Subsequently, a phosphate buffer solution containing 4 mg·mL$^{-1}$ bovine serum albumin was prepared as a blocking agent solution, and this solution was added dropwise onto the measurement region and the reference region on which the antibodies were immobilized (lines 3 and 2 in FIGS. 2A and 2B) and further another region in the reference region (a portion corresponding to line 1 in FIGS. 2A and 2B) and dried.

The prepared chip for optical analysis was mounted on a prism of a surface plasmon resonance measurement device via a matching oil. A phosphate buffer solution containing human IgG was added dropwise onto a sample introduction section of the passage of the chip for optical analysis as a liquid sample. Human IgG, a substance to be measured in the liquid sample, is adsorbed to dextran microparticles in the adsorption region, the phosphate buffer solution not containing human IgG reaches to the observation region, and SPR is observed. The angle of SPR observed in the reference sample not containing human IgG serves as a base level for measurement.

Subsequently, after the adsorbent region is saturated by the liquid sample is further added dropwise, or substance to be measured is prevented from being adsorbed to the adsorbent by protecting (or covered) the adsorption region with a plastic or the like, a large volume of the liquid sample is introduced through the sample introduction section, and thus the liquid sample containing human IgG reaches the measurement region, and human IgG binds selectively to anti-human IgG in the measurement region. On the other hand, the both regions of the region on which anti-goat IgG was immobilized and the region on which only a blocking agent was immobilized in the reference region do not bind to human IgG. Therefore, at this stage, the angle of SPR increases only in the measurement region (a portion corresponding to line 3 in FIGS. 2A and 2B), and the angle of SPR only slightly increases in the reference region (lines 2 and 1 in FIGS. 2A and 2B) as shown in FIG. 7. The difference between the measurement region (line 3) and the region on which anti-goat IgG was immobilized (line 2) in the reference region represents selective binding of human IgG to anti-human IgG, and human IgG can be quantified from these changes over time in the increase in the angles.

Since dextran microparticles adsorb proteins other than IgG, this example is suitable for preparation of reference samples in which various proteins are free. Specifically, dextran microparticles can be used as adsorbents when proteins other than IgG, a substance to be measured, are to be removed, or proteins other than IgG are to be measured as substances to be measured.

Example 3

This example is a chip for optical analysis with a passage having a bypass passage as shown in FIGS. 3A and 3B using a protein A adsorbent as an adsorbent.

Cellulose acetate was dissolved in an organic solvent to prepare a cellulose acetate solution. A gold thin film (thickness 50 nm) was formed on a BK7 glass substrate by vapor-deposition. A resist membrane or a tape was applied onto this gold thin film, and a pattern in which portions of the gold thin film corresponding to the main passage and the bypass passage were exposed was formed. The patterned gold/glass substrate was mounted on a spin coater, the previously prepared cellulose acetate solution was added dropwise, then the substrate was rotated, and the organic solvent was evaporated to form white membrane-form main passage and bypass passage. Subsequently, a buffer solution of protein A was prepared and added dropwise onto an adsorption region of the passage, and protein A was adsorbed to the passage to form the adsorption region. An aqueous solution of carbodiimide was added dropwise onto the region to which protein A was adsorbed and dried to activate the region beforehand. Thus, a passage having a length of 10 mm, a width of 1 mm, a thickness of 1 µm was formed with a bypass passage having a total length of 8 mm.

Subsequently, a small volume of a phosphate buffer solution containing 100 µg·mL$^{-1}$ anti-human IgG (0.1 M, pH 6.8) was added dropwise onto a portion corresponding to a measurement region of the main passage (a portion corresponding to line 3 in FIGS. 3A and 3B) and dried to immobilize the antibody. Similarly, a phosphate buffer solution containing 100 µg·mL$^{-1}$ anti-goat IgG was added dropwise to a portion adjacent to the region in which anti-human IgG was immobilized (a portion corresponding to line 2 in FIGS. 3A and 3B) and dried to immobilize a reference antibody.

Subsequently, a phosphate buffer solution of 4 mg·mL$^{-1}$ bovine serum albumin was prepared as a blocking agent solution, and this solution was added dropwise onto the measurement region and the reference region in which the antibodies were immobilized (lines 3 and 2 in FIG. 3A and 3B) and further another region in the reference region (a portion corresponding to line 1 in FIGS. 3A and 3B).

The prepared chip for optical analysis was mounted on a prism of a surface plasmon resonance measurement device via a matching oil. The phosphate buffer solution containing human IgG was added dropwise onto the sample introduction section of the passage of the chip for optical analysis as a liquid sample. Human IgG that is a substance to be measured in the liquid sample is adsorbed to protein A in the adsorption region, the phosphate buffer solution not containing human IgG reaches the observation region, and SPR is observed. The SPR angle observed in this reference sample not containing human IgG serves as a base level for measurement.

Meanwhile, the liquid sample containing human IgG, which was allowed to flow through the bypass passage, reaches the measurement region after the reference sample reaches the measurement region, and human IgG selectively binds to anti-human IgG in the measurement region. On the other hand, the both regions of the region on which anti-goat IgG was immobilized and the region on which only the blocking agent in the reference region was immobilized do not bind to human IgG. Therefore, at this stage, the SPR angle increases only in the measurement region (a portion corresponding to line 3 in FIGS. 3A and 3B), and the SPR angle only slightly increases in the reference region (a portion corresponding to lines 2 and 1 in FIGS. 3A and 3B) as shown in FIG. 7. A difference between the measurement region (line 3) and the region on which anti-goat IgG was immobilized in the reference region (line 2) represents selective binding of human IgG to anti-human IgG, and human IgG can be quantified from these changes over time in the increase in the angles.

Since the sample containing a substance to be measured reaches the observation region via the bypass passage, when a sample with low viscosity which progresses in the passage rapidly is to be measured, a time lag can be adjusted by providing the bypass passage shown in this example, so that the liquid sample containing the substance to be measured reaches the observation region after the reference sample reaches the observation region. Furthermore, since a protein A adsorbent has a property of selectively coupling to the Fc region of IgG as shown in this example, this example is suitable for preparation of a reference sample by removing only IgG from the sample.

Example 4

This example is a chip for optical analysis with a passage having a bypass passage as shown in FIGS. 3A and 3B using a dextran microparticle adsorbent as an adsorbent.

A cellulose acetate solution was prepared by dissolving cellulose acetate in an organic solvent, and this cellulose acetate solution and modified dextran microparticles (obtained from the microparticlation of methacrylate-modified dextran by radical polymerization) (diameter 15 to 30 μm) were mixed to prepare a cellulose acetate-dextran microparticle mixture solution. A gold thin film (thickness 50 nm) was formed on a BK7 glass substrate by vapor-deposition. A resist membrane or a tape was applied onto this gold thin film, and a pattern in which a portion of the gold thin film corresponding to a passage was exposed was formed. At this time, a portion corresponding to an adsorption region of the passage on the metal thin film was prevented from being exposed, and the cellulose acetate solution was prevented from being deposited on the adsorption region. Subsequently, the patterned gold/glass substrate was mounted on a spin coater, the previously prepared cellulose acetate solution was added dropwise, then the substrate was rotated, and the organic solvent was evaporated to form a white membrane-form passage. Subsequently, the previously prepared cellulose acetate-dextran microparticle mixture solution was added dropwise onto the adsorption region and dried to form the adsorption region so as to connect to the previously formed white membrane-form passage. Thus, a passage having a length of 10 mm, a width of 1 mm, and a thickness of 1 μm was formed with a bypass passage having a full length of 8 mm.

Subsequently, a small amount of a phosphate buffer solution containing 100 μg·mL$^{-1}$ anti-human IgG (0.1 M, pH 6.8) was added dropwise onto a measurement region of the main passage (a portion corresponding to line 3 in FIGS. 3A and 3B) and dried to immobilize the antibody. Similarly, a phosphate buffer solution containing 100 μg·mL$^{-1}$ anti-goat IgG was added dropwise onto a portion adjacent to the region on which anti-human IgG was immobilized (a portion corresponding to line 2 in FIGS. 3A and 3B) and dried to immobilize a reference antibody.

Subsequently, a phosphate buffer solution of 4 mg·mL$^{-1}$ bovine serum albumin was prepared as a blocking agent solution, and this solution was added dropwise onto the measurement region and the reference region on which the antibody was immobilized (lines 3 and 2 in FIG. 3A and 3B) and further another region in the reference region (a portion corresponding to line 1 in FIGS. 3A and 3B) and dried.

The prepared chip for optical analysis was mounted on a prism of a surface plasmon resonance measurement device via a matching oil. The phosphate buffer solution containing human IgG was added dropwise onto the sample introduction section of the passage of the chip for optical analysis as a liquid sample. Human IgG, a substance to be measured in the liquid sample, is adsorbed to protein A in the adsorption region, the phosphate buffer solution not containing human IgG reaches the observation region, and SPR is observed. The SPR angle observed in this reference sample not containing human IgG serves as a base level for measurement.

Meanwhile, the liquid sample containing human IgG, which was allowed to flow through the bypass passage, reaches the measurement region after the reference sample reaches the measurement region, and human IgG selectively binds to anti-human IgG in the measurement region. On the other hand, the both regions of the region on which anti-goat IgG was immobilized and the region on which only the blocking agent was immobilized in the reference region do not bind to human IgG. Therefore, at this stage, the SPR angle increases only in the measurement region (a portion of line 3 in FIG. 2) and the SPR angle only slightly increases in the reference region (portions corresponding to lines 2 and 1 in FIGS. 3A and 3B) as shown in FIG. 7. A difference between the measurement region (line 3) and the region on which anti-goat IgG was immobilized in the reference region (line 2) represents selective binding of human IgG to anti-human IgG, and human IgG can be quantified from these changes over time in the increase in the angles.

Since the sample containing a substance to be measured reaches the observation region via the bypass passage, when a sample with low viscosity which progresses in the passage rapidly is to be measured, a time lag can be adjusted by providing the bypass passage shown in this example, so that the liquid sample containing the substance to be measured reaches the observation region after the reference sample reaches the observation region. Furthermore, since the dextran microparticles adsorb proteins other than IgG in this example, it is suitable for preparation of a reference sample in which various proteins are free. Specifically, when proteins other than IgG, a substance to be measured, are to be removed, or proteins other than IgG are substances to be measured, dextran microparticles can be used as an adsorbent.

Example 5

This example is intended to determine what is suitable as a combination of substances having molecular selectivity used in the measurement region and the reference region.

A cover seal 1034 provided with two openings 1030, 1032 was attached onto a BK7 glass substrate (length 16 mm×width 16 mm) on which a gold thin film (thickness about 50 nm) was formed by vapor-deposition as shown in FIG. 18(*b*). A phosphate buffer solution of anti-human IgG(Fc) extracted from a goat and a phosphate buffer solution of anti-rabbit IgG(Fc) extracted from a goat were added dropwise into these openings 1030 and 1032, respectively, and allowed to stand at room temperature for 20 min or longer. After this process, the solution was sucked, and the cover seal was peeled off to prepare a chip I.

Similarly, using a gold/glass substrate with a cover seal provided with two openings 1030, 1032, a phosphate buffer solution of anti-human IgG extracted from a goat was added dropwise into the opening 1030, allowed to stand at room temperature as described above, and subjected to a posttreatment to prepare chip II, a phosphate buffer solution of anti-human IgG(Fc) extracted from a goat was added dropwise into the opening 1030, a phosphate buffer solution of anti-human IgG(Fab) extracted from a goat was added dropwise into the opening 1032, and these solutions were treated in the same manner as described above to prepare chip III, and a phosphate buffer solution of anti-human IgG (Fc) extracted from a goat was added dropwise in the opening 1030, and a phosphate buffer solution of anti-enterotoxin IgG(Fc) extracted from a rabbit was added dropwise in to the opening 32, and these solutions were treated in the same manner as described above to prepare chip IV.

Each of the prepared chips was mounted on a surface plasmon resonance measurement device (Patent Document 1), and a flow cell made of PDMS was attached on top of the chip as shown in FIG. 21. A liquid sample supplied from a micro syringe pump is introduced into the flow cell via a tube. Furthermore, the device was set, so that the type of a liquid sample could be switched instantly by using a liquid switch in combination.

Figure 22:
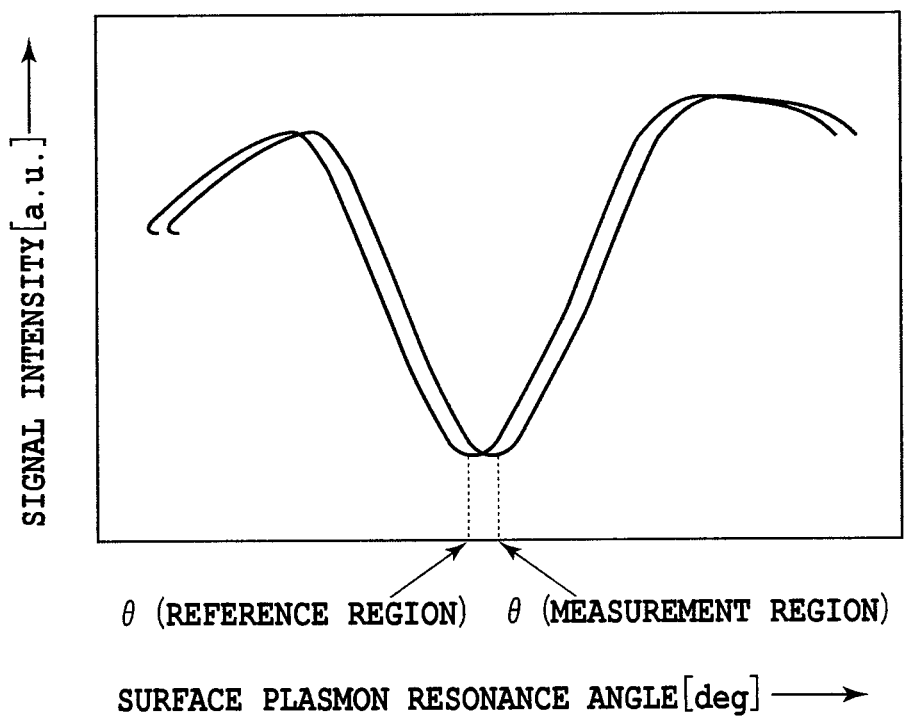
FIG. 22 is a graph showing the relationship between resonance angles and signal intensity when a surface plasmon resonance was measured in the measurement region and the reference region of the chip for optical analysis.

A portion corresponding to the opening 1030 on the substrate was used as a measurement region 1003, and the portion corresponding to the opening 1032 was used as a reference region 1004. When a surface plasmon resonance is measured in these two regions, resonance angles (θ(measurement region), θ(reference region)) can be obtained from the measurement results as shown in FIG. 22. When a change in these resonance angles over time is measured, {θ(measurement region)−θ(reference region)}/time [deg·s$^{-1}$] represented by the difference of these resonance angles represents a difference between the two regions in activity of a substance having molecular selectivity.

When commercially available cow's milk is introduced as a liquid sample containing impurities into the chip set using a flow cells, lipids, casein, proteins, and the like contained in the cow's milk are adsorbed and accumulated in an observation section on which an antibody is immobilized and the gold surface on which the antibody is not immobilized. When a time to allow cow's milk to flow is extended, a resonance angle measured in the surface plasmon resonance device is increased.

When human IgG antigen, which is not contained in cow's milk, is mixed in cow's milk as a substance to be measured, the increasing rate [deg~s$^{-1}$] of θ(measurement region) in the measurement region on which the anti-human IgG is immobilized is expected to exceed the increasing rate [deg~s$^{-1}$] of θ(reference region). When an antigen having a low concentration at the level of several nanograms per mL is measured, a signal in the order of 10$^{-6}$ [deg·s$^{-1}$] is obtained. Therefore, the baseline needs to be limited to the level of 10$^{-6}$ [deg·s$^{-1}$] or lower. In this example, the baseline is a difference generated when cow's milk not containing anti-human IgG, that is, cow's milk alone is introduced to the chip.

Figure 23:
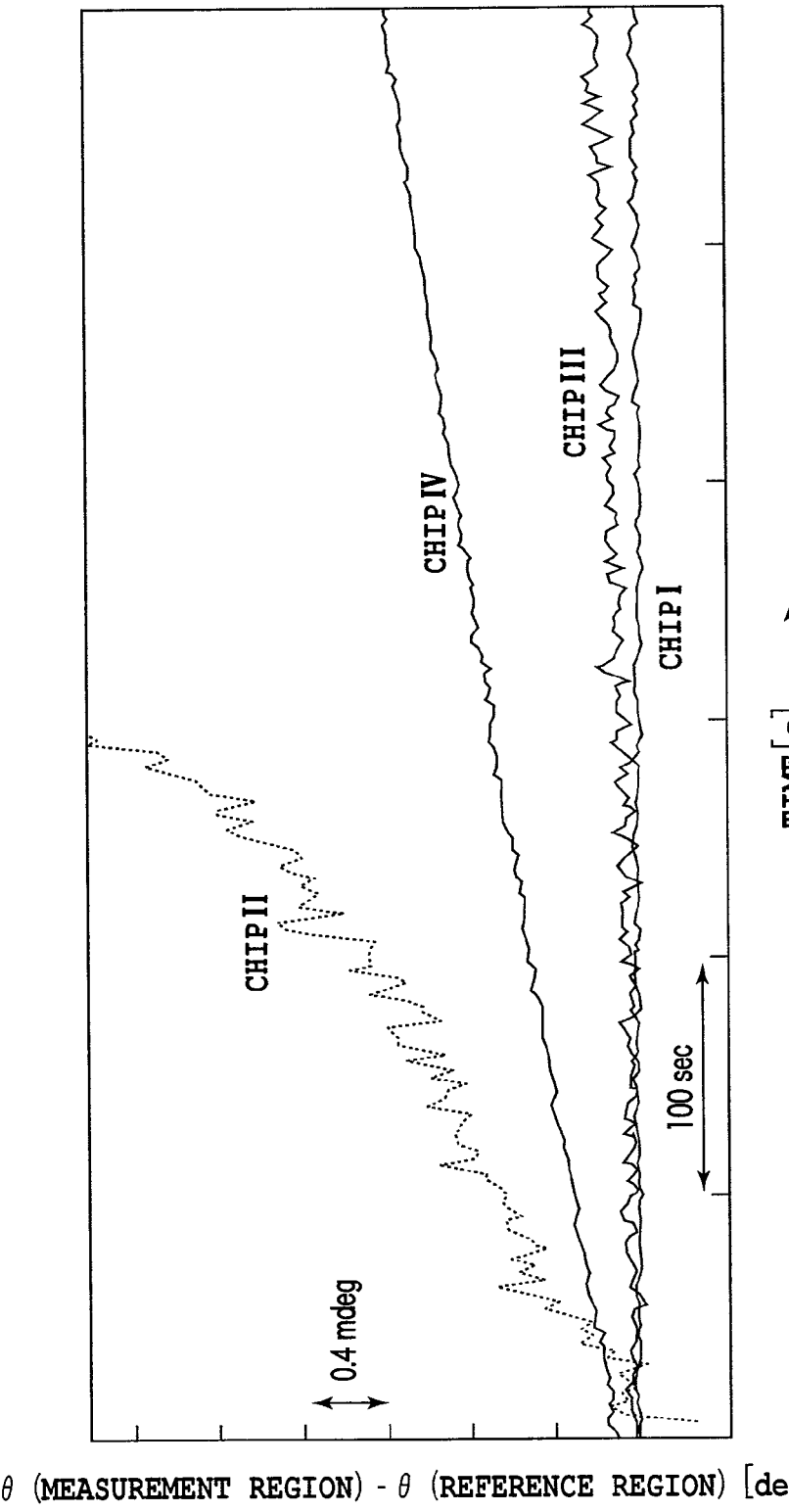
FIG. 23 is a graph showing the relationship between time and $\{\theta(\text{measurement region})-\theta(\text{reference region})\}$ when a surface plasmon resonance was measured in the chips for optical analysis I, II, III, and IV.

When measurement was made using the chips II, III, and IV, the baseline was changed in the range of 10$^{-5}$ to 10$^{-4}$ [deg·s$^{-1}$]. On the other hand, the baseline was limited to 10$^{-6}$ [deg·s$^{-1}$] or lower using the chip I (see FIG. 23).

Thus, by using the Fc regions, which have an equal physical size as IgG antibody, of IgG of the same line which are extracted from the same animal and are different only in selectivity as antibodies for both the measurement region and the reference region, changes in the baseline caused by adsorption and accumulation of impurities as a noise when a liquid sample containing many impurities is measured can be minimized.

Example 6

Using a gold/glass substrate having a cover seal provided with two openings 1030, 1032, a phosphate buffer solution of anti-human IgG extracted from a goat was added dropwise into these two openings 1030, 1032, and only a portion corresponding to the reference region of the opening 1032 was irradiated with an electron beam to decrease selectivity of the antibody. Otherwise, the same procedure as in Example 5 was performed to obtain a chip for optical analysis V. This chip for optical analysis V was mounted on a surface plasmon resonance device as in Example 5, a flow cell was set, and cow's milk was introduced to measure a surface plasmon resonance. The change in the baseline of differential measurement between the measurement region and the reference region was limited to 10$^{-6}$ [deg·s$^{-1}$] or lower.

Example 7

To prepare a substance having molecular selectivity for the reference region 1004, a phosphate buffer solution of anti-human IgG extracted from a goat was heated in a thermostatic bath at 40° C. for 1 h, and the temperature was returned to room temperature. By this procedure, a phosphate buffer solution of inactivated anti-human IgG was obtained.

Subsequently, using a gold/glass substrate having a cover seal provided with two openings 1030, 1032, a phosphate buffer solution of anti-human IgG extracted from a goat was added dropwise into the opening 1030, and a phosphate buffer solution of previously prepared and inactivated anti-human IgG was added dropwise onto a portion corresponding to the reference region of the opening 1032. Otherwise, the same procedure as in Example 5 was performed to obtain a chip for optical analysis VI. This chip for optical analysis VI was mounted on a surface plasmon resonance device in the same manner as in Example 5, a flow cell was set, and cow's milk was introduced to measure a surface plasmon resonance. The change in the baseline of differential measurement between the measurement region and the reference region was limited to 10$^{-6}$ [deg·s$^{-1}$] or lower.

Example 8

Three openings for forming such a metal thin film as shown in FIG. 19 (a), openings for forming pad sections 1044, 1045, and a mask having openings for joining sections 1046, 1047 were provided on a BK7 glass substrate. Gold thin films 1048, 1049, 1050 were formed through openings by means such as vapor-deposition. Subsequently, the mask was removed, and a cover seal having openings 1051, 1052 was applied to the substrate so that the openings 1051, 1052 should match portions of the gold thin films 1048, 1049 formed at the positions of the openings (FIG. 19 (b)). A phosphate buffer solution of anti-human IgG (Fc) extracted from a goat was added dropwise into these openings 1051, 1052, allowed to stand at room temperature for 20 min, and then removed, and the cover seal was peeled off.

Subsequently, as shown in FIG. 19 (c), a cover seal having an opening 1053 is attached with which a part of the joining sections 1046, 1047 is covered, the pad sections 1044, 1045 are exposed, and the gold thin film 1049 on which anti-human IgG(Fc) extracted from a goat is immobilized and a portion of the gold thin film 1050 on which anti-human IgG(Fc) extracted from a goat is not immobilized are exposed. Here, the openings from which the gold thin film 1049 and the gold thin film 1050 are exposed are in a well shape and can hold a solution. A phosphate buffer solution was added dropwise into the well-shaped opening portions of the substrate formed in this manner. Subsequently, as shown in FIG. 20, a silver-silver chloride reference electrode was arranged so that a tip thereof should be brought into contact with a phosphate buffer solution in the well-shaped openings and connected to a potentiostat. The tip was connected to the potentiostat using the portion of the gold thin film 1049 as an action electrode and the portion of the gold thin film 1050 as a counter electrode. Subsequently, a potential cycle of sweeping a potential applied to the action electrode from −0.3 to 1.2 [V vs. silver-silver chloride reference electrode] and returning from 1.2 to −0.3 [V vs. silver-silver chloride reference electrode] was given using the potentiostat and a function generator. By application of this potential cycle, anti-human IgG (Fc) extracted from a goat on the metal thin film 1049 was inactivated. Finally, the reference electrode, the phosphate buffer solution, the cover seal, the potentiostat, the function generator, and the like were removed to obtain a chip for optical analysis VII.

In the same manner as in Example 5, this chip for optical analysis VII was mounted on a surface plasmon resonance device, a flow cell was set, cow's milk was introduced, and a surface plasmon resonance was measured. The change in the baseline in differential measurement between the measurement region and the reference region was limited to $10^{-6}$ [deg·s$^{-1}$] or lower.

Example 9

Using a gold/glass substrate having a cover seal provided with two openings 1030, 1032, a phosphate buffer solution of anti-human IgG extracted from a goat was added dropwise into these two openings 1030, 1032, and a reference buffer at pH 1.68 (Nacarai) was added dropwise into a portion corresponding to the reference region of the opening 1032 to decrease selectivity of the antibody. Otherwise, the same procedure as in Example 5 was performed to obtain a chip for optical analysis VIII. This chip for optical analysis VIII was mounted on a surface plasmon resonance device in the same manner as in Example 5, a flow cell was set, and cow's milk was introduced, and a surface plasmon resonance was measured. The change in the baseline of differential measurement between the measurement region and the reference region was limited to $10^{-6}$ [deg·s$^{-1}$] or lower.

Example 10

Phosphate buffer solutions each containing DNA having the following strand A (SEQ ID NO: 1) or strand B (SEQ ID NO: 2) were prepared. Strand A is DNA for the measurement region, and Strand B is DNA for the reference region.

```
Strand A:
5'-CCT CTG ACT TCA ACA GCG ACA CT-3' (SEQ ID NO: 1)

Strand B:
5'-CCT CAG ACT TCA ACA GGG ACA CT-3' (SEQ ID NO: 2)
```

Using a gold/glass substrate having a cover seal provided with two openings 1030, 1032, a phosphate buffer solution containing strand A was added dropwise into the opening 1030, a phosphate buffer solution containing strand B was added dropwise into the opening 1032, the solutions were sucked in the same manner as in Example 5, and the DNA molecules were immobilized on the gold thin film to obtain a chip for optical analysis X. This chip for optical analysis X was mounted on a surface plasmon resonance device in the same manner as in Example 5, a flow cell was set, and cow's milk was introduced, and a surface plasmon resonance was measured. The change in the baseline of differential measurement between the measurement region and the reference region was limited to $10^{-6}$ [deg·s$^{-1}$] or lower.

Example 11

A chip for optical analysis having a plurality of observation sections was prepared as shown in FIG. 17. A phosphate buffer solution of anti-human IgG(Fc) extracted from a goat and a phosphate buffer solution of anti-rabbit IgG(Fc) extracted from a goat were added dropwise onto the measurement region and the reference region of the observation section 1010, respectively. Furthermore, DNA strands A and B used in Example 10 were added dropwise onto the measurement region and the reference region, respectively, in the observation section 1011. The solution in each region was sucked, and both the antibodies and the DNA molecules were immobilized to obtain a chip for optical analysis XI. This chip for optical analysis XI was mounted on a surface plasmon resonance device in the same manner as in Example 5, a flow cell was set, and cow's milk was introduced, and a surface plasmon resonance was measured. The changes in the baselines in differential measurement between the measurement region and the reference region on which the antibodies were immobilized and the measurement region and the reference region on which the DNA molecules were immobilized were both limited to $10^{-6}$ [deg·s$^{-1}$] or lower.

Example 12

Using the chip for optical analysis I prepared in Example 5, a liquid sample comprising cow's milk containing 50 ng·mL$^{-1}$ of human IgG antigen was introduced into such a measurement device provided with a surface plasmon resonance device and a flow cell as explained in Example 5 to measure a surface plasmon resonance. As a result, as compared with the level of the baseline, a response with a clearly large slope was obtained for a signal represented by {θ(measurement region)−θ(reference region)} (see FIG. 24). The level of the baseline was obtained by measuring cow's milk not containing human IgG before the introduction of the liquid sample.

The above-mentioned results suggest that more human IgG antigen molecules were bound to the measurement region on which anti-human IgG that had not been inactivated was immobilized. On the other hand, the above-mentioned results suggest that selectivity of the inactivated anti-human IgG immobilized on the reference region to human IgG antigen was decreased as compared with the measurement region.

Figure 24:
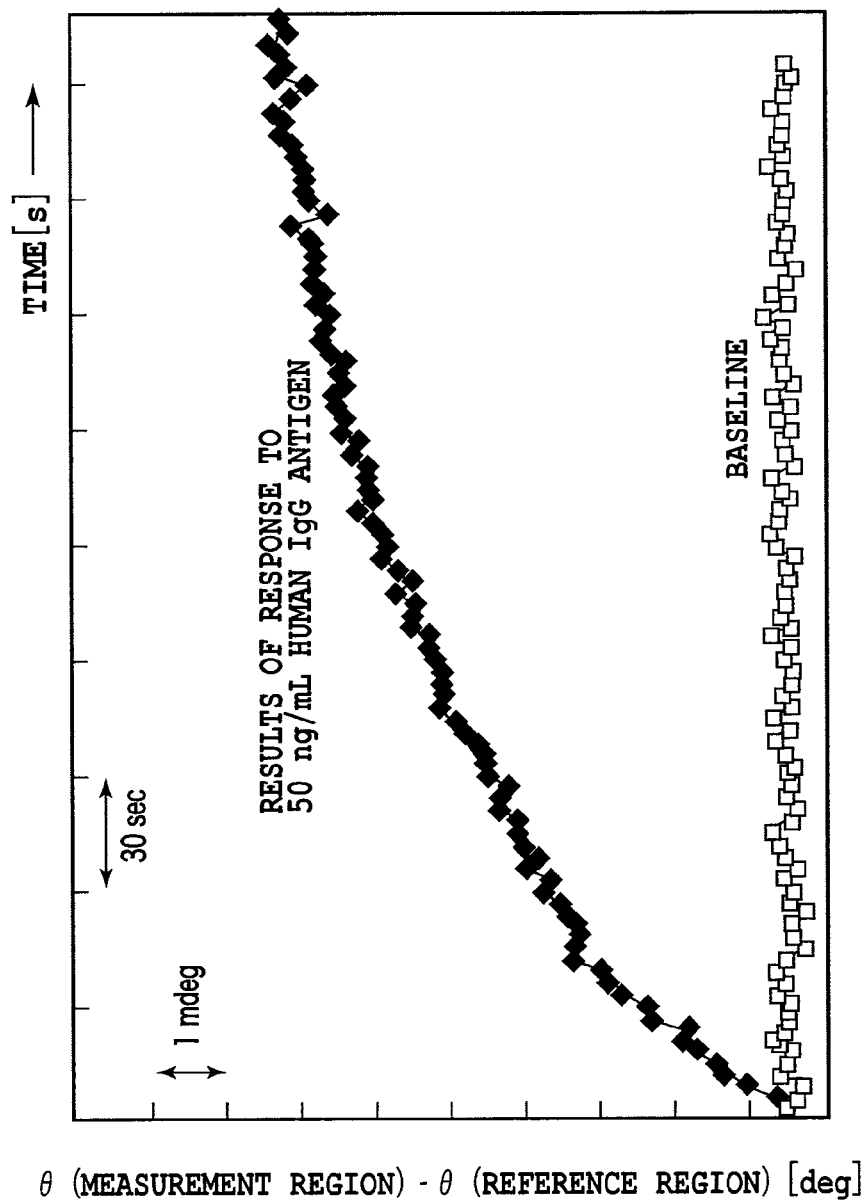
FIG. 24 is a graph showing the relationship between time and $\{\theta(\text{measurement region})-\theta(\text{reference region})\}$ for results of response to an antigen and the baseline when a surface plasmon resonance was measured in the chip for optical analysis I.

Subsequently, using the chips for optical analysis V, VI, VII, and VIII prepared in Examples 6 to 9, a liquid sample comprising cow's milk containing 50 ng·mL$^{-1}$ human IgG antigen was similarly measured for a surface plasmon resonance. As a result of measurement, a response having the same slope as shown in FIG. 24 was obtained. This result suggests that more human IgG antigen molecules were bound to the measurement region on which anti-human IgG antibody that had not been inactivated or subjected to protein engineering was immobilized. On the other hand, the above-mentioned result suggests that selectivity of the inactivated anti-human IgG immobilized on the reference region to human IgG antigen was decreased as compared with the measurement region.

Subsequently, cow's milk containing 1 nmol·mL$^{-1}$ DNA comprising strand C (SEQ ID NO: 3), which forms a specific bond with the strand A, was prepared, and a surface plasmon resonance was measured using the chip for optical analysis X as described above.

```
                                           (SEQ ID NO: 3)
Strand C: 3'-GGA GAC TGA AGT TGT CGC TGT GGG TG-5'
```

As a result, a response with a slope greater than the level of the baseline obtained from cow's milk not containing DNA, 3×10$^{-5}$ [deg·s$^{-1}$], was obtained.

Furthermore, using the chip for optical analysis XI on which antibodies and DNA molecules were immobilized, a surface plasmon resonance of a cow's milk sample containing 50 ng·mL$^{-1}$ human IgG antigen and DNA comprising the strand C was similarly measured. As a result, a response with a slope which was greater than the baseline level and the same as shown in FIG. 24 was obtained for a signal represented by {θ(measurement region)−θ(reference region)} in the observation section on which the antibodies were immobilized, and 3×10$^{-5}$ [deg·s$^{-1}$] that is a response similar to that described above was obtained in the observation section on which DNA molecules were immobilized.

Industrial Applicability

The chip for optical analysis of the present invention can be utilized in an optical measurement method using a total reflection optical system that can directly observe binding of a molecule and an immobilized substance having molecular selectivity.

The invention claimed is:

1. A chip for optical analysis comprising:

a substrate that is transparent to a measurement light;

a chip main body joined to a surface of the substrate;

an introduction port formed on the chip main body for introducing a liquid sample that contains a predetermined component to be measured;

an observation section arranged between the substrate and the chip main body and configured to be irradiated with the measurement light;

a first passage extending between the introduction port and the observation section;

a metal thin film layer positioned on a wall surface of the first passage at the observation section;

a second passage that branches from the first passage at a first position of the first passage such that at the first position, a first portion of the liquid sample introduced at the introduction port flows through the first passage and a second portion of the liquid sample flows into the second passage, the second passage merging back into the first passage at a second position of the first passage, the first and second positions of the first passage being on the upstream side of the observation section such that the second portion of the liquid sample flows back into the first passage and then into the observation section;

an adsorption region for adsorbing the predetermined component to be measured from the first portion of the liquid sample to form a reference sample devoid of the predetermined component to be measured, the adsorption region being positioned in the first passage between the first and second positions so that the second position is between the adsorption region and the observation section, and the adsorption region comprising at least one adsorbent selected from: a dextran gel using protein A as a modifier, an organic membrane-coated silica, and an organic membrane-coated alumina; and means for generating a difference in time to reach the observation section so that the reference sample of the first portion arrives at the observation section through the first passage earlier than the second portion of the liquid sample that passes through the second passage so that optical measurements related to the reference sample can be obtained at the observation section to provide a baseline before the liquid sample arrives at the observation section.

2. The chip for optical analysis according to claim 1, further comprising a liquid absorbing and holding section incorporated in the chip main body, the liquid absorbing and holding section being connected to the first passage on the downstream side of the observation section to absorb the liquid sample and the reference sample that pass through the observation section.

3. The chip for optical analysis according to claim 1, wherein the observation section comprises:
a measurement region for detecting the predetermined component within the liquid sample; and
a reference region.

4. The chip for optical analysis according to claim 1, wherein the means for generating a difference in time to reach the observation section comprises a hydrophilically treated layer formed on a wall surface of the second passage.

5. The chip for optical analysis according to claim 1, wherein the means for generating a difference in time to reach the observation section comprises at least one passage resistance-increasing block projecting from the surface of the substrate into the second passage.

6. The chip for optical analysis according to claim 1, wherein the means for generating a difference in time to reach the observation section comprises a setting of the volume of the second passage larger than that of the first passage from the first position through the second position.

7. The chip for optical analysis according to claim 1, wherein the means for generating a difference in time to reach the observation section comprises a liquid collecting section positioned halfway through the second passage for collecting the liquid sample of the second portion.

8. The chip for optical analysis according to claim 3, wherein a material having molecular selectivity is immobilized on the measurement region in the first passage.

9. The chip for optical analysis according to claim 8, wherein the material having molecular selectivity comprises at least one material selected from the group consisting of an antibody, an antigen, an enzyme, an oligonucleoside, a ribonucleoside, and a modified cyclodextrin compound.

10. The chip for optical analysis according to claim 3, wherein on the measurement region, a first substance having molecular selectivity that selectively interacts with a specific molecule is immobilized, and on the reference region, a second substance having molecular selectivity that is different only in selectivity to the specific molecule with which the first substance having molecular selectivity interacts and is comparable to the first substance having molecular selectivity in other characteristics is immobilized, and the first substance having molecular selectivity and the second substance having molecular selectivity are immobilized on the substrate by the same method.

11. The chip for optical analysis according to claim 10, wherein the first substance having molecular selectivity and the second substance having molecular selectivity are antibodies or antigens of the same kinds.

12. The chip for optical analysis according to claim 10, wherein the second substance having molecular selectivity is obtained by inactivating the first substance having molecular selectivity, and inactivation is achieved by irradiation with a high energy-ray selected from an X-ray, a gamma ($\gamma$)-ray, and an electron beam, heat treatment, electrochemical oxidation or reduction, or contact with an acidic or alkaline buffer.

13. The chip for optical analysis according to claim 10, wherein the first substance having molecular selectivity and the second substance having molecular selectivity are DNA, and the second substance having molecular selectivity is obtained by replacing 10% or less of nucleotides constituting the first substance having molecular selectivity.

14. The chip for optical analysis according to claim 3, wherein a plurality of observation sections each comprising the measurement region and the reference region as one set are provided in the first passage on the substrate, and first substances having molecular selectivity different from each other are immobilized on the measurement region of the observation sections, so that a different molecule can be detected at each observation section.

15. A chip for optical analysis of a predetermined component to be measured, the chip comprising:
a substrate configured to be transparent to a measurement light;
a chip main body joined to a surface of the substrate;
a first passage fluidly extending between a fluid introduction port formed on the chip main body and an observation section formed between the substrate and the chip main body, the first passage including an adsorption region fluidly positioned between the fluid introduction port and the observation section, the adsorption region being configured to adsorb the predetermined component to be measured from fluid that passes therethrough to form a reference sample devoid of the predetermined component to be measured, the adsorption region comprising at least one adsorbent selected from: a dextran gel using protein A as a modifier, an organic membrane-coated silica, and an organic membrane-coated alumina, a metal thin film layer being positioned within the first passage at the observation section;
a second passage fluidly branching from the first passage at a first position of the first passage that is fluidly positioned between the fluid introduction port and the adsorption region, the second passage fluidly reconnecting to the first passage at a second position of the first passage that is fluidly positioned between the adsorption region and the observation section, such that fluid that passes through the second passage bypasses the adsorption region and passes into the observation section after returning to the first passage, the second passage including means for generating a difference in time to reach the observation section such that fluid that passes through the second passage takes a longer amount of time to flow from the first position to the observation section than does fluid that flows through the adsorption region between the first position and the observation section.

16. The chip for optical analysis recited in claim 15, wherein the means for generating a difference in time to reach the observation section comprises a hydrophilically treated layer formed on a wall surface of the second passage.

17. The chip for optical analysis recited in claim 15, wherein the means for generating a difference in time to reach the observation section comprises at least one passage resistance-increasing block projecting from the surface of the substrate into the second passage.

18. The chip for optical analysis recited in claim 15, wherein the means for generating a difference in time to reach the observation section comprises a setting of the volume of the second passage larger than that of the first passage from the first position through the second position.

19. The chip for optical analysis recited in claim 15, wherein the means for generating a difference in time to reach the observation section comprises a liquid collecting section positioned within the second passage.

20. The chip for optical analysis recited in claim 15, further comprising a first substance immobilized on the metal thin film layer, the first substance having molecular selectivity that selectively interacts with a specific molecule.

21. The chip for optical analysis recited in claim 20, further comprising a second substance immobilized on the metal thin film layer, the second substance having molecular selectivity that is different only in selectivity to the specific molecule with which the first substance interacts and is comparable to the first substance in other characteristics.

22. The chip for optical analysis recited in claim 20, wherein the first and second substances are antibodies or antigens of the same kinds.

23. The chip for optical analysis recited in claim 15, wherein the first and second passages are configured such that when a liquid sample having the predetermined component to be measured is introduced at the introduction port:
- the liquid sample flows through the first passage to the first position, where the liquid sample is divided into a first portion and a second portion,
- the first portion flows through the adsorption region of the first passage to form a reference sample that flows to the observation section, the reference sample being devoid of the predetermined component to be measured, and
- the second portion flows concurrently through the second passage and then back into the first passage and on to the observation section so as to bypass the adsorption region, the reference sample arriving at the observation section earlier than the second portion of the liquid sample so that optical measurements related to the reference sample can first be obtained at the observation section to provide a baseline.

* * * * *